US009186435B2

(12) United States Patent
Hiles

(10) Patent No.: US 9,186,435 B2
(45) Date of Patent: *Nov. 17, 2015

(54) EXTRACELLULAR MATRIX COMPOSITE MATERIALS, AND MANUFACTURE AND USE THEREOF

(75) Inventor: Michael C. Hiles, Lafayette, IN (US)

(73) Assignee: Cook Biotech, Incorporated, West Lafayette, IN (US)

( * ) Notice: Subject to any disclaimer, the term of this patent is extended or adjusted under 35 U.S.C. 154(b) by 702 days.

This patent is subject to a terminal disclaimer.

(21) Appl. No.: 12/399,635

(22) Filed: Mar. 6, 2009

(65) Prior Publication Data
US 2009/0204228 A1 Aug. 13, 2009

Related U.S. Application Data

(60) Division of application No. 11/368,077, filed on Mar. 3, 2006, now Pat. No. 7,795,027, which is a continuation of application No. PCT/US2004/029016, filed on Sep. 7, 2004.

(60) Provisional application No. 60/500,026, filed on Sep. 4, 2003.

(51) Int. Cl.
A61F 13/00 (2006.01)
A61L 27/36 (2006.01)
A61K 35/37 (2015.01)
A61L 27/38 (2006.01)
A61L 27/48 (2006.01)
A61K 35/22 (2015.01)
A61K 35/44 (2015.01)

(52) U.S. Cl.
CPC ............ A61L 27/3641 (2013.01); A61K 35/22 (2013.01); A61K 35/37 (2013.01); A61K 35/44 (2013.01); A61L 27/3633 (2013.01); A61L 27/3645 (2013.01); A61L 27/3804 (2013.01); A61L 27/48 (2013.01)

(58) Field of Classification Search
CPC . A61L 27/36; A61L 27/3604; A61L 27/3625; A61L 27/3629; A61L 27/3633
USPC .......................... 424/422, 484, 569, 572, 574
See application file for complete search history.

(56) References Cited

U.S. PATENT DOCUMENTS

| | | | |
|---|---|---|---|
| 2,127,903 A | 8/1938 | Bowen | |
| 4,361,552 A | 11/1982 | Baur | |
| 4,902,508 A | 2/1990 | Badylak et al. | |
| 4,956,178 A | 9/1990 | Baylak et al. | |
| 5,127,903 A | 7/1992 | Mailot et al. | |
| 5,275,826 A | 1/1994 | Badylak | |
| 5,281,422 A | 1/1994 | Badylak et al. | |
| 5,352,463 A | 10/1994 | Badylak et al. | |
| 5,554,389 A | 9/1996 | Badylak et al. | |
| 5,641,518 A | 6/1997 | Badylak et al. | |
| 5,645,860 A | 7/1997 | Knapp et al. | |
| 5,733,337 A | 3/1998 | Carr et al. | |
| 5,770,417 A | 6/1998 | Vacanti et al. | |
| 5,879,383 A | 3/1999 | Bruchman et al. | |
| 5,916,265 A | 6/1999 | Hu | |
| 6,099,567 A | 8/2000 | Badylak | |
| 6,206,931 B1 | 3/2001 | Cook et al. | |
| 6,331,319 B1 | 12/2001 | Badylak et al. | |
| 6,379,710 B1 | 4/2002 | Badylak et al. | |
| 6,485,723 B1 | 11/2002 | Badylak et al. | |
| 6,508,833 B2 | 1/2003 | Pavcnik et al. | |
| 6,572,650 B1 * | 6/2003 | Abraham et al. | ............ 623/1.38 |
| 6,576,618 B1 | 6/2003 | Herndon et al. | |
| 6,582,462 B1 | 6/2003 | Andersen et al. | |
| 6,638,312 B2 | 10/2003 | Plouhar et al. | |
| 6,716,241 B2 | 4/2004 | Wilder et al. | |
| 6,752,828 B2 | 6/2004 | Thornton | |
| 6,783,776 B2 | 8/2004 | Spievack | |
| 6,893,653 B2 | 5/2005 | Abraham et al. | |
| 6,962,814 B2 | 11/2005 | Mitchell et al. | |
| 7,795,027 B2 | 9/2010 | Hiles | |
| 8,409,625 B2 * | 4/2013 | Badylak | ......................... 424/574 |
| 8,454,678 B2 * | 6/2013 | Hiles | ........................... 623/1.24 |
| 2001/0011187 A1 | 8/2001 | Pavcnik et al. | |
| 2001/0039450 A1 | 11/2001 | Pavcnik et al. | |
| 2002/0038151 A1 | 3/2002 | Plouhar et al. | |
| 2002/0123800 A1 | 9/2002 | Taheri et al. | |
| 2002/0188348 A1 | 12/2002 | DiMatteo et al. | |
| 2003/0036794 A1 | 2/2003 | Ragheb et al. | |

(Continued)

FOREIGN PATENT DOCUMENTS

EP 0809691 1/2003
WO WO 95/02611 2/1995

(Continued)

OTHER PUBLICATIONS

Livesey et al. Transplant 1995;60:1-9.*
The Doctors Doctor, Skin Basement Membrane, Apr. 2006 update.*
Hodde et al. Tis Engineering 2002;8(2):225-34.*
Woods, Biomaterials 2004;25:515, Online Abstract page only.*
Oguchi et al. J Invest Dermatol 1985;85:79-81.*
Nguyen et al. J Biol Chem 2000;275:31896-907.*
Badylak et al., "Small Intestinal Submucosa: A Substrate for an in vitro Cell Growth", Journal of Biomaterials Sci. Polymer Edn 1998; 8(9):863-878.

(Continued)

Primary Examiner — Janice Li
(74) Attorney, Agent, or Firm — Woodard Emhardt Moriarty McNett & Henry LLP

(57) ABSTRACT

Described are preferred extracellular matrix composites including a first extracellular matrix material having a second extracellular matrix material deposited thereon. The preferred materials are made by culturing cells in contact with an extracellular matrix graft material in a fashion to cause the cells to biosynthesize and deposit extracellular matrix components on the material. The cells are then removed to provide the extracellular matrix composite material.

28 Claims, 10 Drawing Sheets

(56) References Cited

U.S. PATENT DOCUMENTS

| | | |
|---|---|---|
| 2003/0064056 A1 | 4/2003 | Badylak et al. |
| 2003/0072741 A1 | 4/2003 | Berglund et al. |
| 2003/0125795 A1 | 7/2003 | Pavcnik et al. |
| 2003/0130726 A1 | 7/2003 | Thorpe |
| 2003/0191525 A1 | 10/2003 | Thornton |
| 2003/0208261 A1 | 11/2003 | Thorpe et al. |
| 2003/0216811 A1 | 11/2003 | Badylak |
| 2004/0015230 A1 | 1/2004 | Moll et al. |
| 2004/0049262 A1 | 3/2004 | Obermiller et al. |
| 2004/0082989 A1 | 4/2004 | Cook et al. |
| 2004/0098084 A1 | 5/2004 | Harley et al. |
| 2004/0106978 A1 | 6/2004 | Greenberg et al. |
| 2004/0176832 A1 | 9/2004 | Hartley et al. |
| 2004/0176833 A1 | 9/2004 | Pavcnik et al. |
| 2004/0186558 A1 | 9/2004 | Pavcnik et al. |
| 2004/0260389 A1 | 12/2004 | Case et al. |
| 2005/0025838 A1 | 2/2005 | Badylak |
| 2005/0256588 A1 | 11/2005 | Sawa et al. |
| 2009/0118166 A1 | 5/2009 | Badylak |

FOREIGN PATENT DOCUMENTS

| | | |
|---|---|---|
| WO | WO 96/08213 | 3/1996 |
| WO | WO 96/32146 | 10/1996 |
| WO | WO 98/22158 | 5/1998 |
| WO | WO 98/25636 | 6/1998 |
| WO | WO 99/62431 | 12/1999 |
| WO | WO 01/19285 | 3/2001 |
| WO | WO 02/40630 | 5/2002 |
| WO | WO 03/002165 | 1/2003 |
| WO | WO 03/070124 | 8/2003 |
| WO | WO 2004/022107 | 3/2004 |
| WO | 2004/029016 | 4/2004 |
| WO | WO 2005/023321 | 3/2005 |

OTHER PUBLICATIONS

Clarke, K.M, et al. "Intestine Submucosa and Polypropylene Mesh for Abdominal Wall Repair in Dogs". The Journal of Surgical Research. Jan. 1996. vol. 60, No. 1. pp. 107-114.

Heeschen C., et al., "Nicotine stimulates angiogenesis and promotes tumor growth and atherosclerosis," Nature Medicine 7 (2001). No. 7, 833-839.

Johnson, C. et al. "Matrix Matalloproteinaso-9 is Required for Adequate Angiogenic Revascularization of Ischemic Tissues—Potential Role in Capillary Branching", Circulation Research (2004) 94;262-268. American Heart AssociatiOn, Dallas, TX.

Kropp et al., "Experimental Assessment of Small Intestinal Submucosa as a Bladder Wall Substitute," Urology, Sep. 1995; vol. 46, Issue 3, pp. 396-400.

Kropp et al., "Regenerative Urinary Bladder Augmentation Using Small Intestinal Submucosa: Urodynamic and Histopathologic Assessment in Long-Term Canine Bladder Augmenations," J. Urology, vol. 155, pp. 2098-2104, Jun. 1996.

Lindberg, K. et al., "Porcine Small Intestinal Submudoca (SIS): A Bioscaffold Supporting in Vitro Primary Human Epidermal Cell Differentiation and Synthesis of Basement Membrane Proteins", Burns 27 (2001) 254-266. Elsevier Science Ltd. and ISBI.

Prevel et al., "Small Intestinal Submucosa: Utilization as a Wound Dressing in Full-Thickness Rodent Wounds," Annals of Plastic Surgery, Oct. 1995; vol. 35, No. 4, pp. 381-388. Little Brown and Company.

Prevel, C.D., et al. "Small Intestinal Submucosa: Utilization for Repair of Rodent Abdominal Wall Defects". Annals of Plastic. Surgery. Oct. 1995. vol. 35, No. 4. pp. 374-380.

Woods, A.M. et al., "Improved Biocompatibility of Small Intestinal Submucosa (SIS) Following Conditioning by Human Endothelial Cells", Biomaterials 24 (2004) 515-525. Elsevier, Ltd.

Xie et al., "Use of Reconstructed Small Intestine Submucosa for Urinary Tract Replacement," ASAIO Journal, May-Jun. 2000; vol. 46, No. 3, pp. 268-272.

Gospodarowicz rt al, "Comparison of the Ability of Basement membranes Produced by Corneal Endothelial and Mouse-derived Endodermal PF-HR-9 Cells to Support the Proliferation and Differentiation of Bovine Kidney Tubule Epithelial Cells in Vitro," J Cell Biol 1984;947-61.

Lindberg et al. "Porcine small intestinal submucosa (SIS): a bioscaffold supporting in vitro primary human epidermal cel differentiation and synthesis of basement membrane proteins" Burns 2001; 27:254-66.

Voytik-Harbin et al. "Small Intestinal Submucosa: A Tissue-Derived Extracellular Matrix That Promotes Tissue-Specific Growth and Differentiation of Cells in Vitro," Tissue Engineer 1998; 4:157-74.

\* cited by examiner

EXTRACELLULAR MATRIX COMPOSITE MATERIALS, AND MANUFACTURE AND USE THEREOF

REFERENCE TO RELATED APPLICATIONS

This application is a divisional application of U.S. patent application Ser. No. 11/368,077, filed Mar. 3, 2006, now U.S. Pat. No. 7,795,027 which is a continuation application of International Application No. PCT/US2004/029016 filed Sep. 7, 2004 (which was published in English), which claims the benefit of U.S. Patent Application Ser. No. 60/500,026 filed Sep. 4, 2003, each of which is hereby incorporated by reference in its entirety.

BACKGROUND OF THE INVENTION

The present invention relates generally to medical graft materials, and in particular to medical graft materials having extracellular matrix materials deposited thereon.

By way of further background, a variety of extracellular matrix materials have been proposed for use in medical grafting, cell culture, and other related applications. For instance, medical grafts and cell culture materials containing submucosa derived from small intestine, stomach or urinary bladder tissues, have been proposed. See, e.g., U.S. Pat. Nos. 4,902, 508, 4,956,178, 5,281,422, 5,554,389, 6,099,567 and 6,206, 931. In addition, Cook Biotech Incorporated, West Lafayette, Ind., currently manufactures a variety of medical products based upon small intestinal submucosa under the trademarks SURGISIS®, STRATASIS® and OASIS®.

Medical materials derived from liver basement membrane have also been proposed, for example in U.S. Pat. No. 6,379, 710. As well, ECM materials derived from amnion (see e.g. U.S. Pat. Nos. 4,361,552 and 6,576,618) and from renal capsule membrane (see WO003002165 published Jan. 9, 2003) have been proposed for medical and/or cell culture applications.

Despite work in these areas there remain needs for alternative and improved materials, methods and devices related to ECM materials. The present invention addresses these needs.

SUMMARY OF THE INVENTION

In one aspect, the present invention provides a material, desirably a medical graft material, comprising a substantially acellular extracellular matrix composite including a first extracellular matrix material having a surface, and a second, biosynthetically-deposited extracellular matrix material on said surface. The second, biosynthetically-deposited extracellular matrix material is non-native to the surface of the first extracellular matrix material, i.e., it is added to the surface of the first extracellular matrix material as opposed to being retained from the source of the first extracellular matrix material. In certain forms, the inventive composite material is substantially devoid of both cells and cell components.

In another aspect, the present invention provides a method for inducing endogenous tissue growth in an animal, including the step of implanting in the animal a medical graft material as described above.

The present invention also provides a method for culturing cells, which involves culturing the cells on an extracellular matrix composite material as described above.

The present invention also provides a method for making an extracellular matrix composite, comprising the steps of (a) providing a first extracellular matrix material having a surface; (b) culturing cells in vitro under conditions to secrete extracellular matrix components wherein said components are transferred to said surface to form an extracellular matrix composite comprising said first extracellular matrix material with said extracellular matrix components on said surface; and (c) decellularizing the extracellular matrix composite.

The present invention provides novel materials useful for medical grafting and cell culture, and methods for making and using them. Additional embodiments as well as features and advantages of the invention will be apparent from the descriptions herein.

Figure 10:
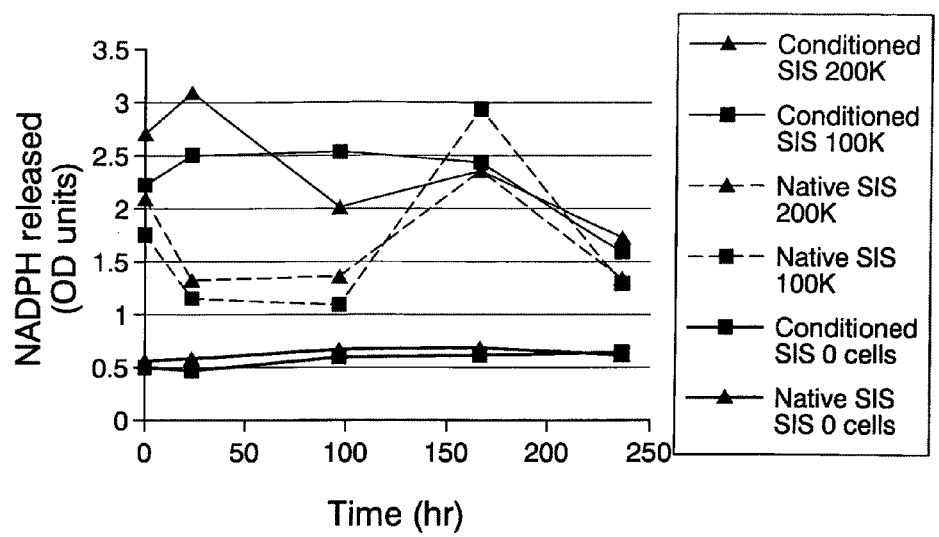
Figure 11:
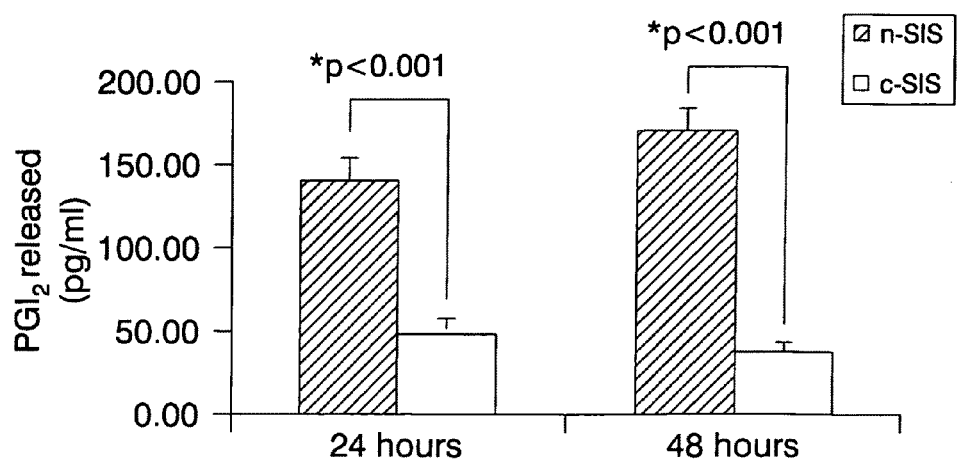

FIG. 10. NADPH production is greater at 24 and 96 h after plating in HUVEC grown on conditioned SIS compared to native SIS. Metabolic activity assays that measure the production of NADPH by cells were carried out with native and conditioned SIS onto which 100,000 or 200,000 cells/cm2 were seeded for 1-240 h. At 24 and 96 h after seeding, NADPH production by HUVEC grown on conditioned SIS was significantly higher than by cells grown on native SIS. At the 168 h time point there was no difference between the groups. Note that error bars have been omitted to simplify the appearance of the graph. Conditioned vs. native at 24 and 96 h, $p<0:005$:

FIG. 11. Prostacyclin ($PGI_2$) release from HUVEC is lower when cells are grown on conditioned SIS compared to cells grown on native SIS. HUVEC were seeded at 100,000 cells/cm2 on native and conditioned SIS and grown for 24 or 48 h. After 24 or 48 h the media was replaced and HUVEC were cultured for an additional 1 hand $PGI_2$ in the media was measured. HUVEC grown on conditioned SIS released significantly less prostacyclin ($p<0:0001$) compared to cells grown on native SIS at both 24 and 48 h time points.

FIG. 12. Adhesion of human platelets is lower on conditioned SIS compared to native SIS. Adhesion of resting (A) or thrombin activated (B) human platelets labeled with 51Cr was measured on native SIS and conditioned SIS. Platelet adhesion was significantly reduced by 40.4% when resting platelets were used, and by 29.6% when thrombin-activated activated platelets were used. *$p<0:05$ vs native SIS.

DESCRIPTION OF THE PREFERRED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and modifications in the illustrated device and method, and further applications of the principles of the invention as illustrated therein are herein contemplated as would normally occur to one skilled in the art to which the invention relates are included.

As disclosed above, the present invention provides medical grafting materials including extracellular matrix composites, and methods for their manufacture and use. As used herein, the term "acellular" means free or essentially free from living cells. The term "substantially devoid of cells and cell components" means free or essentially free from cells (living or dead) and of cell membranes and other cell remnants. An ECM material substantially devoid of cells or cell components is intended to include the ECM material carrying cells or cell components at a level sufficiently low to be non-immunogenic when the material is implanted in a recipient, especially a recipient to which the cells or cell components are xenogenic or allogenic. The term "decellularizing" in respect of a cell-containing ECM material means that the material is treated to as to remove at least about 70% of the original cells (living or dead). More preferably, at least 90% of the cells will be removed, and most preferably at least 99% of the cells will be removed, in decellularization processes involved in the instant invention.

Medical grafting devices and methods of the invention employ a first extracellular matrix (ECM) base material. Preferred are naturally-derived collagenous ECMs isolated from suitable animal or human tissue sources. Suitable extracellular matrix materials include, for instance, submucosa (including for example small intestinal submucosa, stomach submucosa, urinary bladder submucosa, or uterine submucosa, each of these isolated from juvenile or adult animals), renal capsule membrane, amnion, dura mater, pericardium, serosa, peritoneum or basement membrane materials, including liver basement membrane or epithelial basement membrane materials. These materials may be isolated and used as intact natural sheet forms, or reconstituted collagen layers including collagen derived from these materials and/or other collagenous materials may be used. For additional information as to submucosa materials useful in the present invention, and their isolation and treatment, reference can be made to U.S. Pat. Nos. 4,902,508, 5,554,389, 5,733,337, 5,993,844, 6,206,931, 6,099,567, and 6,331,319. Renal capsule membrane can also be obtained from warm-blooded vertebrates, as described more particularly in International Patent Application serial No. PCT/US02/20499 filed Jun. 28, 2002, published Jan. 9, 2003 as WO03002165.

Preferred ECM base materials contain residual bioactive proteins or other ECM components derived from the tissue source of the materials. For example, they may contain Fibroblast Growth Factor 2 (basic FGF), vascular endothelial growth factor (VEGF), and Transforming Growth Factor-beta (TFG-beta). It is also expected that ECM base materials of the invention may contain additional bioactive components including, for example, one or more of glycosaminoglycans, glycoproteins, proteoglycans, and/or growth factors.

In accordance with one embodiment of the invention, cells will be cultured in vitro on the ECM material under conditions and for a duration wherein secreted extracellular matrix proteins are deposited upon a portion of or the entire surface of the ECM material. After deposition of the desired amount of extracellular matrix proteins, the resulting ECM composite material can be isolated by decellularizing the material. The deposited ECM proteins may, for example, enhance the functionality of the ECM base material, e.g. by potentially affecting remodeling of the material by cells and/or the thrombogenicity of the material. In addition, after seeding, e.g. during culture, the ECM base material along with seeded cells can be subjected to mechanical, chemical or physical stresses to influence the cell growth and deposition products. Such forces could include but are not limited to mechanically stretching the ECM base material, preferably without tearing it, subjecting the ECM base material to pulsatile forces (e.g. by flowing fluid such as culture medium through a tube of ECM base material), altering the culture atmosphere, e.g. to a higher or lower carbon dioxide content, or adding specific growth factors or chemokines that affect the cell growth rates, phenotypes, secretory functions or apoptosis events, thereby affecting the molecules deposited by the cells.

Cells to be used to secrete ECM proteins can be applied to the surface of the base ECM supporting structure in any suitable fashion. Illustratively, the cells can be applied to the base ECM material by allowing gravity to settle the cells onto the base ECM. Positive pressure may also be used to force media through the ECM material, thereby depositing cells onto the ECM surface. Other suitable means for applying the cells to the ECM may include, but not be limited to using negative pressure to draw the cells onto the ECM material; and using chemotactic agents, for example.

As to the type and source of the cells to be used to deposit ECM components onto the ECM base material, a variety of cell types, or combinations of cell types, may be used. These cell types are known to those of ordinary skill in the art, as are appropriate conditions for their culture. Illustratively, cell types to produce the ECM proteins for deposition include vascular and other endothelial cells (including microvascular endothelial cells), vascular and other smooth muscle cells, fibroblasts, corneal endothelium or epithelium, glomerular epithelium, and mesothelial cells, pericytes, macrophages, monocytes, plasma cells, mast cells, adipocytes, chondrocytes, etc. These other cells can be readily derived from appropriate organs or tissues such as skin, liver, etc., using methods known, such as those discussed above. Alternatively or in addition, cells from established cell lines of any of the above-mentioned or other suitable types may be used to deposit the ECM components. Cells of cardiovascular origin, and in particular vascular endothelial cells, are preferred, used alone or in combination with vascular smooth muscle cells.

Illustratively, vascular smooth muscle cells (SMCs) can be isolated from segments of carotid or femoral arteries obtained from humans (e.g. the patient to be treated or cadaver) or animals. Such isolation procedures are known and may for example involve storing the tissue segments in a suitable sterile medium, such as sterile Medium 199 (Gibco BRL) potentially also containing antibiotic agents such as gentamicin. The artery segment can be slit longitudinally and the endothelial cells removed by rubbing and/or scraping (e.g. with a scalpel blade). Thin strips of arterial media peeled up with forceps are pooled into HBSS in a sterile Petri dish. The strips can then be cultured in tissue culture flasks containing a suitable culture medium, e.g. Smooth Muscle Cell Growth Medium (SMCGM) (43% Dulbecco's Modified Eagle Medium (DMEM); 43% Medium 199; 13% fetal bovine serum; 2 mM glutamine; 15 units/ml heparin; 23 µg/ml gentamicin; and 12.5 µg/ml endothelial cell growth supplement (Collaborative Biomedical Products, Bedford, Mass.)). The culture medium can be replaced when significant outgrowth of cells from the tissue pieces is observed. The cells can then be fed the SMCGM periodically as needed, and conventionally passaged and split. Smooth muscle cell type can be confirmed, for instance by morphological criteria, positive staining for alpha smooth muscle cell actin, and/or other suitable known techniques.

For seeding purposes, subconfluent VSMC cultures can be rinsed with calcium-magnesium-free-HBSS (CMF-HBSS) and washed in CMF-HBSS. Cells can be harvested using trypsin-ethylenediamine tetraacetic acid (EDTA) to release cells from the flask, followed by trypsin neutralization with SMCGM. Cells can be pelleted by centrifugation and the pellet re-suspended in SMCGM for cell counting. After centrifugation, the cell pellet can be re-suspended in SMCGM. This cell suspension can then be contacted with the ECM base material to seed the material with the cells. The seeded ECM can then be placed into a culture container filled with SMCGM. The culture container can be capped and incubated at about 37° C. on a roller apparatus. The medium in the culture tubes can be periodically replaced and the seeded ECMs can be cultured for a period sufficient to deposit ECM components, for example, from one to twenty days.

In another embodiment, endothelial cells are used to deposit ECM proteins on an ECM base material. For instance, endothelial cells can be caused to attach and spread on the ECM surface, and cultured to deposit the ECM proteins. For these purposes, small patches of endothelial cells may be directly harvested from a donor vessel (e.g. a vessel of the patient to be treated, or a cadaver) and seeded onto an ECM surface whereby they will attach and proliferate to cover the ECM surface, and deposit ECM components.

In one mode of recovery, enzymatic methods can be used to release endothelial cells (ECs) from arterial or venous vessels obtained from humans or animals. The vessel lumina are cannulated, rinsed with HBSS, and filled with an endothelial cell harvesting enzyme solution in a suitable medium such as CMF-HBSS. Suitable enzymes include, but are not limited to, collagenase, dispase, and trypsin. Endothelial cells are flushed into a sterile centrifuge tube and the ECs pelleted. The cells are then plated onto tissue culture flasks, grown at about 37° C. until nearly confluent and then passaged. Endothelial cell type can be confirmed by morphological criteria, by positive staining for Factor VIII, and by uptake of acetylated low density lipoprotein.

Subconfluent endothelial cells (passages 2-10, for example) can be rinsed with CMF-HBSS and washed in CMF-HBSS. The cells can be harvested by using trypsin-EDTA to release cells from the flasks followed by trypsin neutralization with complete Endothelial Cell Growth Medium (ECGM; 80% Medium 199, 16% fetal bovine serum, 2 mM glutamine, 15 units/ml heparin, 25 µg/ml gentamicin, 12.5 µg/ml Endothelial Cell Growth Supplement (Collaborative Biomedical Products, Bedford, Mass.)). The cells can be pelleted and the pellet re-suspended in ECGM. This suspension can then be used to seed the ECM base material, and then cultured in association with the ECM base material to secrete and deposit the desired amount of ECM components, for example, one to twenty days.

Once a suitable layer of secreted ECM proteins is created, the endothelial cell layer can be removed. For example, the endothelial cells can be removed by rinsing the graft several times (e.g. three times) with HBSS, and treating with an ammonium hydroxide solution, e.g. about 0.025M ammonium hydroxide, to remove the endothelial cells, and rinsed again several times in HBSS. Other suitable treatments may include, for example, 0.01-0.5M ammonium hydroxide for about 30 seconds to about 60 minutes. Other candidate methods of removing the endothelial cells may include air drying, or treatment with other stripping solutions, for example, chloroform, methanol, ammonium hydroxide, or sodium chloride, either alone or in combination. Other treatments known to those skilled in the art may also be suitable.

It is also possible to produce a secreted matrix deposit through a variety of other methods. One suitable method, for example, involves using mixed culture seeding in which both ECs and SMCs are combined and both cell types are seeded onto the ECM base material simultaneously. After extended co-culture, the secreted matrix will be produced.

Fibroblasts for use in depositing extracellular matrix proteins may be readily isolated from an appropriate source organ or tissue. This can be readily accomplished using techniques known to those skilled in the art. For example, the tissue or organ can be disaggregated mechanically and/or treated with digestive enzymes and/or chelating agents that weaken the connections between neighboring cells, making it possible to disperse the tissue into a suspension of individual cells without appreciable cell breakage. Enzymatic dissociation can be accomplished by mincing the tissue and treating the minced tissue with any of a number of digestive enzymes either alone or in combination. Such enzymes include, but are not limited to, trypsin, chymotrypsin, collagenase, elastase, hyaluronidase, DNase, pronase, and/or dispase etc. Mechanical disruption can also be accomplished by a number of methods including, but not limited to the use of grinders, blenders, sieves, homogenizers, pressure cells, insonators, and the like.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting.

In one embodiment of the present invention, cells, which are specialized for the particular tissue implant site, can be cultured on the base ECM material for the production of a tissue type specific extracellular matrix composite. Accordingly, the first ECM material can conditioned to create the ECM composite using cells of a given type, and the resulting ECM composite can be configured for and grafted on or in a type of tissue of the patient having cells of that given type.

For example, dermal fibroblasts can be used to form the three-dimensional subconfluent stroma for the production of skin-specific extracellular composite matrix in vitro. Alternatively, stromal cells of hematopoietic tissue including, but not limited to, fibroblast endothelial cells, macrophages/monocytes, adipocytes and reticular cells, can be used to form the three-dimensional subconfluent stroma for the production of a bone marrow-specific extracellular matrix in vitro. Hematopoietic stromal cells can be readily obtained from the "buffy coat" formed in bone marrow suspensions by centrifugation at low forces, e.g., 3000×g.

Similarly, glial cells can be used as the stroma to support the proliferation of neurological cells and tissues. Glial cells for this purpose can be obtained by trypsinization or collagenase digestion of embryonic or adult brain.

For certain uses in vivo it may be preferable to obtain the cells from the subject's own tissues. The growth of cells in the presence of the ECM base material can be further enhanced by adding to the framework, or coating the framework support with natural or recombinant molecules, including but not limited to, proteins, such as collagens, elastic fibers, reticular fibers, and glycoproteins; glycosaminoglycans, such as heparin sulfate, chondroitin-4-sulfate, chondroitin-6-sulfate, dermatan sulfate, keratan sulfate, etc.; a cellular matrix, and/or other materials, such as whole blood, serum, growth factors, fibronectin, Pronectin F, RGD peptide, or cell or tissue extracts.

Stem cells may also be used and cultured on the ECM base material to deposit extracellular matrix components. Illustratively, adult or embryonic stem cells may be cultured and treated with appropriate differentiation factors to mature and secrete extracellular matrix components. The differentiated cell population can then be removed using suitable techniques as described herein.

After inoculation with the cells, the ECM base material is incubated in an appropriate nutrient medium under physiologic conditions favorable for cell growth, i.e., promoting mitosis (cell division). Many commercially available media such as RPMI 1640, Fisher's, Iscove's, McCoy's, and the like, may be suitable for use. The three-dimensional culture can be suspended or floated in the medium during the incubation period in order to maximize proliferative activity. In addition, the culture can be "fed" periodically to remove the spent media, depopulate released cells, and to add fresh media.

During the incubation period, the cells are grown to an appropriate degree to allow for adequate deposition of extracellular matrix components. The extracellular matrix components are secreted locally by cells and not only bind cells and tissues together but also influence the development and behavior of the cells they contact. The typical extracellular matrix contains various fiber-forming proteins interwoven in a hydrated gel composed of a network of glycosaminoglycan chains. The glycosaminoglycans are a heterogeneous group of long, negatively charged polysaccharide chains, which (except for hyaluronic acid) are covalently linked to protein to form proteoglycan molecules.

The fiber-forming proteins are of two functional types: (a) mainly structural (collagens and elastin), and (b) mainly adhesive (such as fibronectin and laminin). The fibrillar collagens (types I, II, and III) are rope-like, triple-stranded helical molecules that aggregate into long cable-like fibrils in the extracellular space; these in turn can assemble into a variety of highly ordered arrays. Type IV collagen molecules assemble into a sheetlike meshwork that forms the core of all basal laminae. Elastin molecules form an extensive cross-linked network of fibers and sheets that can stretch and recoil, imparting elasticity to the matrix.

Fibronectin and laminin are examples of large adhesive glycoproteins in the matrix; fibronectin is widely distributed in connective tissues, whereas laminin is found mainly in basal laminae. By means of their multiple binding domains, such proteins help cells adhere to and become organized by the extracellular matrix.

As an example, a naturally secreted human dermal extracellular matrix contains type I and type III collagens, fibronectin, tenascin, glycosaminoglycans, acidic and basic FGF, TGF-beta, KGF, decorin and various other secreted human dermal matrix proteins. As naturally secreted products, the various extracellular matrix proteins are produced in the quantities and ratios similar to that existing in vivo. Moreover, growth of the stromal cells in three dimensions will sustain active proliferation of cells in culture for much longer time periods than will monolayer systems. Further, the three-dimensional system supports the maturation, differentiation, and segregation of cells in culture in vitro to form components of adult tissues analogous to counterparts found in vivo. Thus, the extracellular matrix created by the cells in culture is more analogous to native tissues.

As disclosed above, the ECM composite material will be decellularized after deposition of the desired level of non-native ECM components on the ECM base material. In an illustrative decellularization process, the tissue may be treated with a solution that releases component cells from the associated extracellular membrane matrix. There are a number of agents and methods that will remove the cells. The cell-containing composite material can be treated with a mild chemical stripping solution, such as ammonium hydroxide ($NH_4OH$). One such treatment may involve incubating the material in an aqueous $NH_4OH$ solution at a concentration of about 0.01M to about 0.5M, for a period of about 30 seconds to about 60 minutes followed by flushing the vessel lumen or other ECM construct with a buffer solution. Illustratively, the treatment may involve treating the cell-containing material with a 0.25M $NH_4OH$ solution for about 1 to 10 minutes.

Decellularization may also involve air drying. Following air drying, the material can be flushed with buffer to remove cells and cell components and rehydrate the ECM composite for further processing, if desired.

The cells can also be removed by exposing the cell-containing material to one or more freeze-thaw cycles, typically followed by removal of dead cells and cell debris. For example, such removal may be accomplished by flushing the material after freezing with a suitable solution such as HBSS (1.3 mM $CaCl_2$, 5 mM KCl, 0.3 mM $KH_2PO_4$, 0.5 mM $MgCl_2$, 0.4 mM $MgSO_4$, 138 mM NaCl, 4 mM $NaHCO_3$, 0.3 mM $NaHPO_4$, 5.6 mM glucose). Freeze-kill of the cells may be accomplished, for instance, by flash-freezing the living cells in liquid nitrogen.

The cells may also be killed by irrigating the inoculated three-dimensional framework with sterile water, such that the cells burst in response to osmotic pressure. Once the cells have been killed, one can, for example, disrupt the cellular membranes and remove the cellular debris by a mild detergent rinse, such as EDTA, CHAPS or a zwitterionic detergent, followed by treatment with a cryoprotectant such as DMSO, propylene glycol, butanediol, raffinose, polyvinyl pyrrolidone, dextran or sucrose and vitrified in liquid nitrogen.

Alternatively, the cell-containing material can be subjected to enzymatic digestion and/or extracting with reagents that break down the cellular membranes and allow removal of cell contents. Examples of detergents include non-ionic detergents (for example, TRITON X-100, octylphenoxy polyethoxyethanol, (Rohm and Haas); BRIJ-35, a polyethoxyethanol lauryl ether (Atlas Chemical Co.), TWEEN 20, a polyethoxyethanol sorbitan monolaureate (Rohm and Haas), LUBROL-PX, or polyethylene lauryl ether (Rohm and Haas)); and ionic detergents (for example, sodium dodecyl sulphate, sulfated higher aliphatic alcohol, sulfonated alkane and sulfonated alkylarene containing 7 to 22 carbon atoms in a branched or unbranched chain). Enzymes can be used also and can include nucleases (for example, deoxyribonuclease and ribonuclease), phospholipases and lipases.

Following removal of the cells, the ECM composite material can be treated with a fixative, if desired. This fixation can be accomplished by placing the graft into a fixing solution, such as, for example, glutaraldehyde in a suitable buffer. Suitable buffers may include, but are not limited to, N-2-hydroxyethylpiperazine-N'-2-ethane sulfonic acid (HEPES), acetate, 2-(N-morpholino) ethanesulfonic acid (MES), 3-[N-morpholino] propanesulfonic acid (MOPS), tris hydroxymethyl aminomethane, phosphate, and others. Any remaining aldehyde reactive sites can be blocked with an amino group containing solution. Suitable reagents for this procedure include, but are not limited to, 0.1M glycine, Medium 199, Dulbecco's Modified Eagle Medium, and other physiological culture media, for example.

ECM composite graft materials of the invention can be manufactured in a variety of physical forms, to suit a variety of medical applications. For example, the graft materials may be formed as sheets, tubes, or other three-dimensional shapes. In this regard, the configuration of the ECM composite material may be attained before or after deposition of the non-native ECM components on the ECM base material. Further, an ECM composite material can be manufactured in larger, bulk dimensions, and then divided into smaller products. Moreover, the ECM base material may provided in a naturally-derived layer form, or may itself be a manufactured article, such as a sponge or cast sheet, prepared from a naturally-derived ECM material.

ECM composite grafts of the invention may be used in a wide variety of medical (including veterinary) applications. Examples of specific tissues which can be repaired and/or reconstructed using the inventive ECM composite materials included nervous tissue, skin, cardiovascular tissue (including vascular tissue and cardiac tissue), pericardial tissue, muscle tissue, ocular tissue, periodontal tissue, bone, connective tissue such as tendons or ligaments, and others.

In specific embodiments of the invention, it is contemplated that the ECM composites of the present invention can be formed into grafts taking the forms of powders, fluidized compositions, sheets, tubes, pouches, multi-ply constructs, single-ply constructs, and constructs in combination with other medical devices or implements such as stents, valves, catheters, sutures, staples, balloons, metal coils, synthetic meshes, biodegradable polymers, inert polymers, non-biodegradable polymers, other collagenous matrices, stem cells, vectors for gene delivery, other naturally-occurring, synthetic, or recombinant bioactive molecules, or in combination with other combinations of these medical devices or implements.

Illustratively, the ECM composites of the present invention can be formed into a powder tissue graft composition. The ECM composite material can be comminuted by tearing, cutting, grinding, shearing or the like, frozen or not, in a manner similar to that described for other collagen-based ECMs in U.S. Pat. No. 5,275,826, International Publications Nos. WO 96/32146, WO 98/22158 and WO 98/25636; the disclosures of which are expressly incorporated herein by reference. Grinding the ECMs in a frozen or freeze-dried state is advantageous, although good results can be obtained as well by subjecting a suspension of pieces of the ECMs to treatment in a high speed blender and dewatering, if necessary, by centrifuging and decanting excess waste. The comminuted ECMs can then be dried, for example freeze dried, to form a powder.

In orthopedic applications, ECM composite powders of the invention can be used to repair bone tissue, for instance using the general techniques described in U.S. Pat. No. 5,641,518. Thus, a powder form of the ECM composite can be implanted into a damaged or diseased bone region for repair. The ECM composite powder can be used alone, or in combination with one or more additional bioactive agents such as physiologically compatible minerals, growth factors, antibiotics, chemotherapeutic agents, antigen, antibodies, enzymes, vectors for gene delivery and hormones. Preferably, the powder-form implant will be compressed into a predetermined, three-dimensional shape, which will be implanted into the bone region and will substantially retain its shape during replacement of the graft with endogenous tissues.

The ECM composites of the invention may be fluidized following techniques as described in U.S. Pat. No. 5,275,826, the disclosure of which is incorporated herein by reference. Fluidized form of the composite ECMs are generally prepared by solubilization by enzymatic digestion, including the use of protease, such as trypsin or pepsin, or other appropriate enzymes such as a collagenase or a glycosaminoglycanase, or the use of a mixture of enzymes, for a period of time sufficient to solubilize the tissue and form a substantially homogeneous solution. While a fluidized composition may be formed from enzyme digestion of comminuted tissues, a procedure involving only enzyme digestion with no mechanical commination can also be used.

The ECM composites can be provided as sheet constructs. For example, the ECM composites can be spread out into a native sheet form, trimmed to size if desired, and lyophilized. Multi-layer sheet constructs can be made including two or more such sheets stacked directly atop one another. In this regard, these constructs can be stabilized by bonding the collagen sheets together, for example by compressing the sheets under dehydrating conditions, use of crosslinkers, or other suitable means.

Larger area sheet constructs can be prepared by overlapping and fusing together of several smaller area ECM sheets. The construction of a large area sheet from smaller area sheets has been described in U.S. Pat. No. 5,127,903, International Publication No. WO 96/32146, and ASAIO Journal, 2000, 46:268-272. In one embodiment, the small area sheets are fused together by compressing the overlapped edges of these sheets under dehydrating conditions. In another embodiment, the sheets are joined by photocrosslinking in the presence of a photo-catalytic dye. Other standard tissue bonding techniques known to those skilled in the art, including the use of sutures, crosslinking agents, adhesives and pastes can also be used. The smaller area sheets can be bonded or fused together to form a larger area sheet before or after the deposition of the non-native ECM components and decellularization steps described above.

The composite ECM matrices can be configured into tubes of various dimension and thickness to provide tubular tissue grafts useful in, for example, vascular, urinary tract or nervous system repair or replacement. As one specific example, tubular grafts may be used in coronary artery and peripheral artery replacement, or the like, e.g. with the graft having an internal diameter of about three to six millimeters. Techniques for making tubular grafts from collagenous sheets have been generally described in U.S. Pat. Nos. 2,127,903 and 4,902,508 and International Publication No. WO 98/22158, the disclosures of which are expressly incorporated herein by reference. Illustratively, a tubular graft may be constructed by manipulating sheets of the ECMs to define a tube and suturing, bonding or otherwise securing the longitudinal seam to form an appropriately-dimensioned tubular graft having a lumen. In addition, the tube may be formed so as to present a lumenal and/or outer surface comprising the deposited ECM material. In one embodiment, the tubular construct is formed over a sterile rod or mandrel having an outer diameter approximating that of the recipient vessel to be grafted. Preferably, at least one sheet layer of the inventive ECM composite is wrapped about the rod to form an overlapping seam. The overlapped seam may be joined together by any of the conventional methods such as suturing, photocrosslinking, radiation crosslinking, fusion under compression and dehydration, or by adhesive and the like. It is further understood that the tubular grafts may be constructed from multiple layers of ECMs, with the number of layers used generally depending on the strength requirement of the particular application. For example, vascular grafts can be constructed with multiple layers of ECM sheets to ensure that they can withstanding the constant pulsating pressure of their implanting environment. For vascular, urinary tract, or other body lumen applications, composite ECMs of the invention can be used as exterior, interior or other coverings for supporting structures such as stents, grafts, etc. These applications include, for example, use with self-expanding or otherwise expandable stents, both to form biocompatible coverings such as sleeves and to form leaflets or other valve structures (see, e.g. WO9962431 published Dec. 9, 1999 and WO119285 published Mar. 22, 2001, both hereby incorporated herein by reference). In one mode of forming a valve structure, the ECM composite material can be attached to a stent in a fashion whereby it forms one, two, or more leaflets, cusps, pockets or similar structures that resist flow in one direction relative to another. In a specific application of such devices, such devices constructed as vascular valves are implanted to treat venous insufficiencies in humans, for example occurring in the legs. In an alternate approach, valves for treating these or other valve deficiencies may be surgically created without the use of a stent or other supporting structure.

Figure 1:
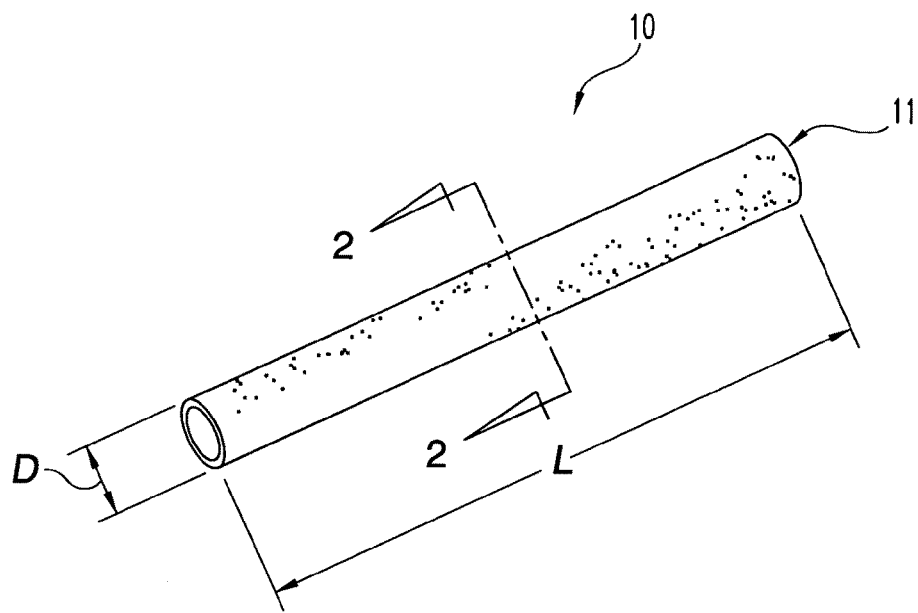
FIG. 1 provides a perspective view of a tubular graft prosthesis device of the present invention.
Figure 2:
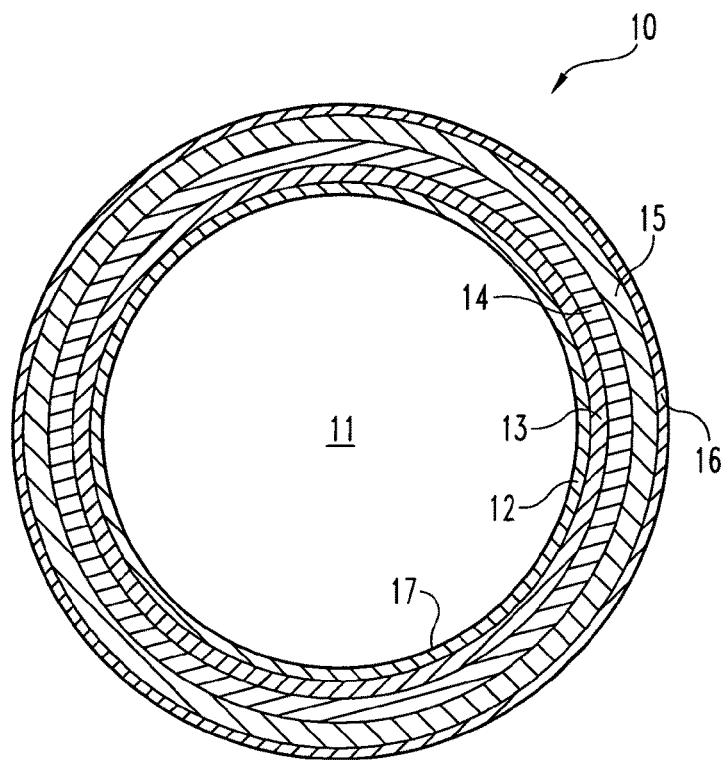
FIG. 2 provides a cross-sectional view of the tubular graft prosthesis device depicted in FIG. 1 taken along line 2-2 and viewed in the direction of the arrows.

Tubular grafts containing the ECM composite material of the invention may also be prepared as disclosed in International Publication No. WO 2004/022107 published Mar. 18, 2004, which claims the benefit of U.S. Patent Application Ser. No. 60/408,914 filed Sep. 6, 2002 and entitled TISSUE GRAFT PROSTHESIS DEVICES CONTAINING JUVENILE OR SMALL DIAMETER SUBMUCOSA, each of which is incorporated herein by reference in its entirety. All or some of the layers of the disclosed tubular grafts may contain an ECM composite material of the present invention, and in particular embodiments at least the lumenal surface of the tubular constructs will contain the second ECM material. In this regard, a pre-manufactured ECM composite material may be fashioned into such disclosed constructs, or the overall construct may be prepared including the first ECM material, and then the second ECM material deposited onto the first ECM material followed by decellularization as disclosed herein. Briefly, and with reference to FIGS. 1-3, shown is a perspective view of a tubular graft prosthesis 10. Tubular graft prosthesis 10 defines an inner lumen 11 and has a length L and diameter D rendering the construct suitable for the intended use, for example a vascular use.

With reference now to FIGS. 1 and 2 together, shown in FIG. 2 is a cross-sectional view of the prosthesis 10 of FIG. 1 taken along line 2-2 and viewed in the direction of the arrows. Prosthesis 10 has walls defining inner lumen 11, preferably including several layers of material as illustrated. In particular, shown in prosthesis 10 is a first tubular layer 12, a second layer tubular layer 13, a third tubular layer 14, a fourth tubular layer 15, and a fifth tubular layer 16. At least one of these layers may include juvenile submucosa from a warm-blooded vertebrate animal, or otherwise include an intact tubular submucosa segment having a small native internal diameter (12 mm or less). The animal is preferably a mammal, such as a porcine, ovine, bovine, or other mammalian animal. Human donor tissues may also be used in the present invention. In the case of juvenile porcine submucosa, the animal at harvest will typically not exceed about 10 kilograms (kg).

In certain aspects of the invention, the juvenile or other small diameter submucosa tissue will retain its intact, tubular form as harvested from the animal. More preferably, at least the innermost layer 12 will be formed from intact, tubular juvenile submucosa tissue. In this fashion, the surface 17 of the lumen 11 will be defined by the intact juvenile submucosa tissue, and will be free of any seams that would otherwise be created when configuring sheet-form tissue into a tube. Preferred devices will include at least one additional layer, for example, layers 13, 14, 15 and 16 as illustrated in FIG. 2. These additional layers can be made of any suitable material and desirably provide reinforcement and strength to the device supplemental to that provided by innermost layer 12. When innermost layer 12 is comprised of juvenile submucosa tissue, one or more of layers 13, 14, and 15 may, for example, be formed of synthetic materials such as synthetic polymer materials. Suitable synthetic materials may be biodegradable or non-biodegradable materials. These include, for example, synthetic biocompatible polymers such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof, polylactic acid, polyglycolic acid or copolymers thereof, a polyanhydride, polycaprolactone, polyhydroxy-butyrate valerate, polyhydroxyalkanoate, or another biodegradable polymer.

In certain embodiments of the invention where layer 12 is comprised of juvenile submucosa, one or more of, and potentially all of layers 13, 14, 15 and/or 16 are formed from additional collagenous materials. For example, suitable collagenous materials include extracellular matrix layers including, for instance, submucosa, renal capsule membrane, dura mater, pericardium, serosa, peritoneum or basement membrane layers, including liver basement membrane. These layers may be isolated and used as intact membranes, or reconstituted collagen layers including collagen derived from these materials or other collagenous materials may be used.

Desirably, layers 13, 14, 15 and 16 are made from additional submucosa tissue layers. Suitable submucosa tissues for these purposes include, for instance, intestinal submucosa including small intestinal submucosa, stomach submucosa, urinary bladder submucosa, and uterine submucosa. Small intestinal submucosa, when employed, can be used in an intact, native tubular form or can be a tubular form shaped from flat sheets including one or more seams along all or a portion of its length. Desirably, at least one of layers 13, 14, 15 and 16 will include adult submucosa tissue, as such tissue in its native condition is generally superior in mechanical properties to juvenile submucosa tissue. In this fashion, adult submucosa tissue can be used to provide strength to the overall graft construct 10. Porcine small intestinal submucosa is particularly preferred for these purposes.

In one form, intermediate layers 14 and 15 can be made from adult small intestinal submucosa, and intermediate layer 12 and outermost layer 16 can be made from juvenile small intestinal submucosa, preferably again in its native, intact tubular form. In this fashion, seamless inner layer 12 and seamless outer layer 16 can be provided.

Layers 12, 13, 14, 15 and 16 can be adhered to one another so as to generally form a unitary construct. This adherence may be achieved, for example, by crosslinking, including for example dehydrothermal crosslinking or chemical crosslinking, and/or by the use of a bonding agent. As bonding agents for these purposes, one may use fibrin glue, or gelatin or collagenous pastes in sufficient amount to bond adjacent layers to one another.

Tubular devices of the invention may be prepared, for example, by positioning the appropriate tissue layers over a mandrel, and subsequently bonding or adhering the tissue layers together to form a generally unitary tubular construct. This may be accomplished, for instance, using intact tubes, and/or by wrapping or winding sheet- or strip-form adult submucosa tissue around the mandrel to form overlapped sections which are subsequently bonded or adhered. In some embodiments, an outermost covering layer may be provided by an intact juvenile submucosa segment positioned over the underlying tissue layers. If a bonding agent is to be used in forming the construct, the agent or its components can be applied at appropriate points intermediate the application of layers to the mandrel. The entire construct can then be dried, e.g., lyophilized and/or dried under vacuum, to form the overall tubular graft construct.

In some embodiments of the invention, tubular prosthesis devices are prepared using a two component bonding agent such as fibrin glue (e.g., having thrombin and fibrinogen as separate components). To prepare such devices, subsequent layers are added after coating the previously-applied layer with a first component of the bonding agent (e.g., thrombin) and coating a layer to be applied with a second component of the bonding agent (e.g., fibrinogen). Thereafter, the layer to be applied is positioned over the previously-applied layer so as to bring the two bonding components into contact, thus causing the curing process to begin. This process can be repeated for any and all additional layers to be applied to the tubular construct.

Figure 3A:
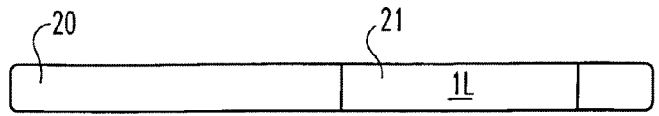
FIGS. 3A-3G depict steps used in the manufacture of a 5-layer tubular prosthesis device of the invention.
Figure 3B:
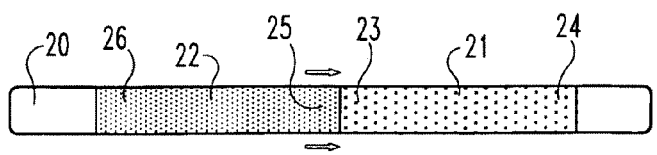
Figure 3C:
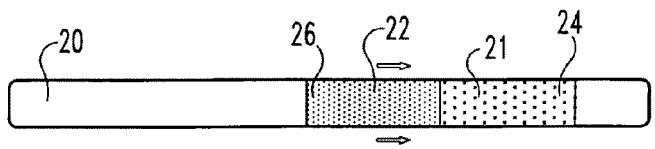
Figure 3D:
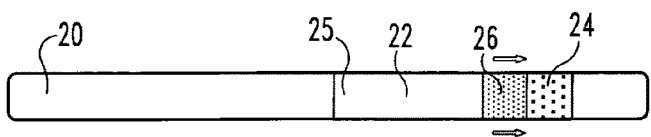
Figure 3E:
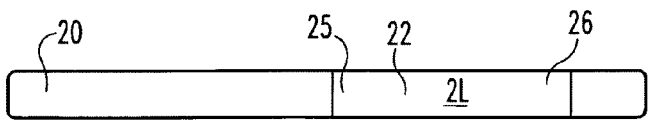
Figure 3F:
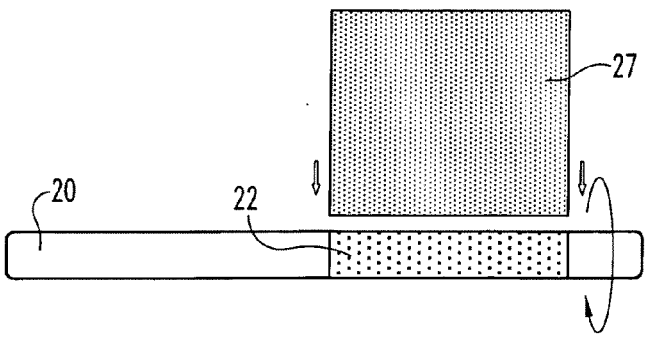
Figure 3G:
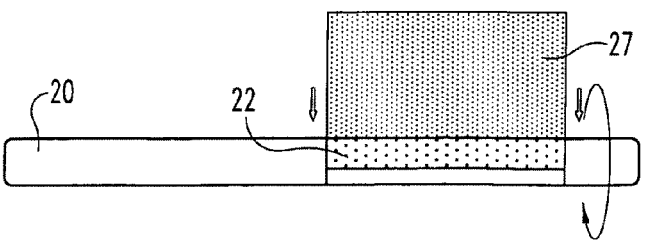
Figure 3H:
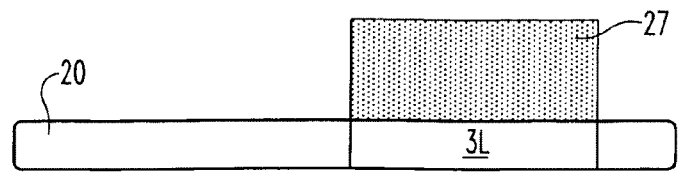
Figure 3I:
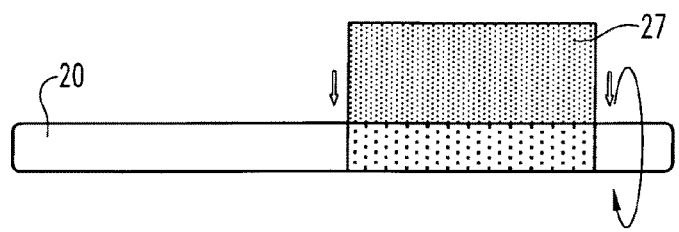
Figure 3J:
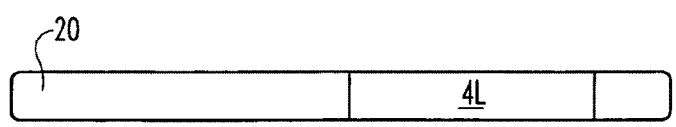
Figure 3K:
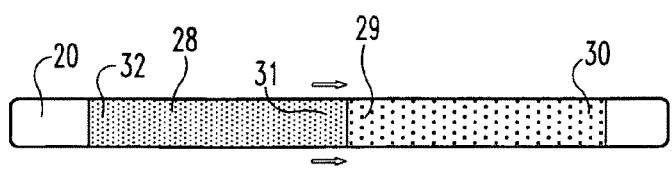
Figure 3L:
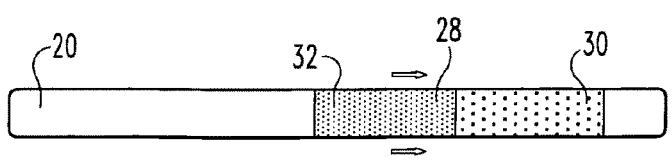
Figure 3M:
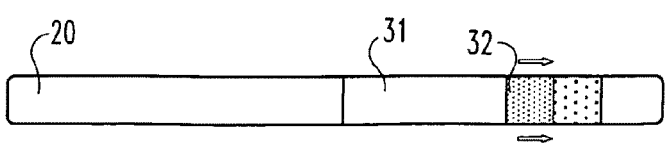
Figure 3N:
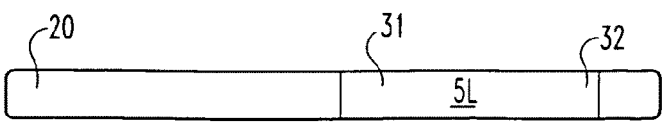

With reference now to FIGS. 3A through 3G, an illustrative manufacture of a 5-layer (5L) tubular device of the invention will now be described. An intact tubular submucosa segment 21 from a juvenile animal may first be positioned over a mandrel 20 as depicted in FIG. 3A, to provide a one-layer (1L) construct. Thrombin (light shading, FIG. 3B) is then applied to the intact segment 21. A second intact tube of juvenile submucosa 22 is provided either on an extension of the same mandrel as illustrated, or on a second mandrel connectable to the first mandrel. The second intact segment 22 is coated with fibrinogen (dark shading), and the segment 22 is positioned immediately adjacent the first segment 21. Segment 22 is then and pulled over the first submucosa tube in a fashion causing inversion of the tube 22 (FIGS. 3C-3E). Thus, leading end 25 of segment 22 remains substantially in place, but inverted, in contact with the trailing end 23 of segment 21. Trailing end 26 of segment 22 finally inverts and comes into contact with leading end 24 of the first segment 21. In this fashion, portions of the two submucosa tubes coming together will remain substantially together, i.e., one submucosa layer will not pulled along another submucosa layer. This is beneficial in that as the bonding agent begins to cure, movement of submucosa layers relative to one another becomes difficult. The inversion of the second tube is continued until it is completely inverted and lying atop the first submucosa tube, creating a two-layer (2L) construct as illustrated in FIG. 3E. The fibrin glue of the 2L construct is then allowed to cure (typically 1 to 5 minutes). The outer surface of the 2L construct is coated with thrombin (light shading, FIG. 3F). Fibrinogen (dark shading, FIG. 3F) is then applied to one surface of a sheet 27 of adult submucosa of a dimension sufficient to encircle the prior-applied layers two times. As illustrated in FIGS. 3F-3H, the adult submucosa is then wrapped around the 2L construct for a single turn (clockwise rotation in FIGS. 3F-3G), resulting in a completed three-layer (3L) construct on the mandrel 20. During or after curing of the applied fibrin glue components, thrombin is applied to the outer surface of the 3L construct (light shading, FIG. 3I). A second turn of the adult submucosa sheet 27 is then completed (FIG. 3I), bringing the applied thrombin and fibrinogen components into contact with one another, and forming the completed four-layer device (4L, FIG. 3J). During or after cure of the newly-contacted fibrin glue components, a third intact tubular juvenile submucosa segment 28 (FIG. 3K) is positioned adjacent to the applied layers, thrombin (light shading) is coated onto the 4L construct and fibrinogen (dark shading) is coated onto the third tubular segment 28. The third tubular segment 28 is then pulled and inverted over onto the applied layers (FIGS. 3K-3M) as before to complete the 5L construct (FIG. 3N), with the leading end 31 of the third segment 28 lying atop the trailing end 29 of segment the 4L construct, and the trailing end 32 of segment 28 lying atop the leading end 30 of the 4L construct. The device is then allowed to cure and is trimmed as necessary. It will be understood that the application of thrombin and fibrinogen or any other two-components for the bonding agent could be reversed in order. As well, the components of the bonding agents can be applied by any suitable method, including spray or brush application methods, and intermediate constructs can be hydrated at appropriate points in the manufacture. The entire construct may then be freeze-dried or otherwise processed (e.g. to deposit the second ECM material on lumenal or other surfaces) if desired.

ECM composite matrices of the invention can optionally be preconditioned for orthopedic or other applications, again before or after deposition of ECM components and removal of the depositing cells. Preparation of orthopedic grafts have been generally described in U.S. Pat. Nos. 2,127,903; 5,281, 422; 5,275,826; and 5,352,463, the disclosures of which are expressly incorporated herein by reference. Conditioning alters the viscoelastic property and reduces the strain inherent in the native ECMs sheets. The ECMs may be conditioned by stretching, chemical treatment, enzymatic treatment or exposing the tissue to other environmental factors, or any other art known methods. The ECMs can be conditioned by stretching under a load to a predetermined percentage of the pre-stretched length. For example, the ECMs may be conditioned by suspending a weight from a segment of an ECM sheet for a period of time sufficient to allow about 10% to about 20% elongation of the segment. The ECM segment can then be configured, alone or in combination with other segments, to a variety of shapes to serve as orthopedic grafts.

In one area of orthopedic use, ECM composites of the invention can be used for the repair and/or replacement of connective tissues. Such connective tissues include bone, cartilage, tendons and ligaments. For example, the composite ECMs may serve as ligament or tendon replacement or a patch for a broken or severed tendon or ligament.

In connective tissue applications, it may be advantageous to form, manipulate or shape the end portions of the graft construct to be attached, for example, to a bone structure, in a manner that will reduce the possibility of graft tearing at the point of attachment. For these purposes, the conditioned ECM composite graft material can be folded or partially everted to provide multiple layers for gripping, for example, with spiked washers or staples. Alternatively, a ECM material can be folded back on itself to join the end portions to provide a first connective portion to be attached, for example, to a first bone and a bend in the intermediate portion to provide a second connective portion to be attached to a second bone articulated with respect to the first bone. For example, one of the end portions of the ECM graft can be adapted to be pulled through a tunnel in, for example, the femur and attached thereto, while the other of the end portions may be adapted to be pulled through a tunnel in the tibia and attached thereto to provide a substitute for the natural cruciate ligament, the segment being adapted to be placed under tension between the tunnels to provide a ligament function, i.e., a tensioning and position function provided by a normal ligament.

Furthermore, ECM composite sheets of the present invention can also be used to provide an orthopedic graft for use as connective tissue to hold fractured bone pieces together and in proper orientation in the body, the tissue segment being formed to serve as a fracture wrap about segments of fractured bone and to be attached to the bone.

In certain embodiments of the invention, the first ECM (base) material can be disinfected and/or sterilized by contact with a suitable agent such as peracetic acid or another oxidizing disinfectant prior to seeding with the cells to be used to deposit the second ECM material, during removal of such cells, after removal of such cells, or any combination of these. Such disinfection/sterilization techniques may for example be conducted using agents and general conditions as disclosed in U.S. Pat. No. 6,206,931, which is incorporated herein by reference in its entirety.

The ECM composite graft constructs and compositions of the invention can be packaged to protect the purity of the constructs/compositions for storage and shipment to the consumers. In one embodiment, dried graft constructs are packaged in pre-sterilized bags and then vacuum sealed. These packages may be stored and shipped at room temperature. In another embodiment, graft constructs that are in a hydrated state are packaged in pre-sterilized bags and then vacuum sealed. The hydrated samples may be stored and shipped frozen. Preferably, the pre-sterilized bags are formed of materials that are impervious to moisture and oxygen, e.g., PETE. For added assurance that the purity of the construct are maintained, before storage, the sealed packages may be irradiated to decimate pathogens that were inadvertently collected on the surface of the constructs during manufacturing. In yet another embodiment, dried graft constructs can be packaged in non-sterile gas permeable bags and then vacuum-sealed. The packaged constructs are then sterilized along with the gas permeable packaging using ethylene oxide gas. It is contemplated that still other conventional techniques for sterilization which are within the knowledge of those of ordinary skill in the arts may also be used, including for example radiation and plasma sterilization techniques.

Tissue graft compositions including ECM composites of the invention can be administered to a vertebrate host in an amount effective to induce endogenous tissue growth at a site in the host in need of same due to the presence of damaged or diseased tissue. It is contemplated that the vertebrate host may be autogenic, allogenic or xenogenic to the animals from which the base ECMs were harvested, and/or to the cells used to deposit the ECM components on the ECM base material. In certain modes of practicing the invention, the vertebrate host is a human, the ECM base material is allogenic or xenogenic, and the ECM-depositing cells are autogenic, allogenic or xenogenic to the human host. In two specific, advantageous modes of practicing the invention, (1) the base ECM is xenogenic and the ECM-depositing cells are autogenic to the human recipient of the ECM composite graft, and (2) the base ECM is xenogenic and the ECM-depositing cells are human and allogenic to the recipient of the ECM composite graft. In certain instances, it may be advantageous to use immunologically matched (to the recipient) and/or modulated cells to deposit the ECM components on the ECM base material.

Following removal of the cells used to deposit the second extracellular matrix material, the isolated extracellular matrix composite material can be used to prepare a cell-seeded graft, if desired. For example, cells allogenic or autogenic to the recipient of a graft of the composite material can be seeded and optionally proliferated on the composite material, which can then be implanted, along with the cells, into the recipient. Any of the cell types disclosed above for deposit of the second extracellular matrix material can also be used in such cell-seeded grafts, including combinations of such cell types. In certain embodiments of cell-seeded grafts, the first extracellular matrix material will be xenogenic to a human recipient (e.g. of porcine or bovine origin), the second extracellular matrix material will be human but allogenic to the recipient, and the cells of the cell-seeded graft will be autogenic or allogenic to the recipient, and when allogenic optionally either immunologically matched or modulated to minimize potential immune response.

Fluidized composite ECMs of this invention may be used in orthopedic applications, e.g. tissue replacement, augmentation, and/or repair. It is contemplated that fluidized ECMs of the present invention may be used as an injectable heterograft. By injecting an effective amount of a fluidized ECMs composition into the location of a tissue defect, for example, in bone or soft tissues in need of repair or augmentation, one can readily take advantage of the biotropic properties of the ECMs. It is further contemplated that the fluidized composition can be used advantageously as a filler for implant constructs, e.g., in cosmetic or trauma-treating surgical procedures.

Composite ECMs of the invention can also be used in body wall repair, including for example in the repair of abdominal wall defects such as hernias, using techniques analogous to those described in Ann. Plast. Surg., 1995, 35:374-380; and J. Surg. Res., 1996, 60:107-114. In such applications, preferred ECM tissue grafts of the invention promote favorable organization, vascularity and consistency in the remodeled tissue.

In dermatological applications, composite ECMs of the invention can be used in the repair of partial or full thickness wounds and in dermal augmentation using general grafting techniques which are known to the art and literature (see, e.g. Annals of Plastic Surgery 1995, 35:381-388). In addition, in the area of burn treatment, it is generally known to provide a dermal substitute onto which cultured epidermal grafts (preferably cultured epidermal autografts, or CEA's) are transplanted. Such cultured grafts have typically involved transplanting keratinocytes and/or fibroblasts onto the dermal substitute. In accordance with the present invention, the composite ECMs can be used as the dermal substitute, for example in sheet form, and the CEA provided on the composite ECMs. In one embodiment of practicing this aspect of the invention, keratinocytes can be transplanted, for example by seeding or transferring a keratinocyte sheet, onto the denser side of the composite ECM sheet and fibroblasts can be transplanted also on the more areolar side of the composite ECM sheet.

Composite ECMs of the invention can also be used in tissue grafts for urogenital applications. For instance, a large area composite ECM sheet can be used for the repair of urinary bladder, in which the composite ECM sheet provides a scaffold for bladder tissue regeneration. The techniques for urinary bladder repair have been generally described in U.S. Pat. No. 5,645,860; Urology, 1995, 46:396-400; and J. Urology, 1996, 155:2098; the disclosures of which are incorporated herein by reference.

Tubular grafts including composite ECMs may be used for the repair and replacement of the urinary tract. A tubular graft of a specific diameter and strength, the making of which has been previously described, can be surgically substituted for a damaged or diseased urinary tract by standard surgical techniques. Technique for urinary tract replacement has been described generally in "Use of Reconstructed Small Intestine Submucosa for Urinary Tract Replacement", by Xie et. al, in ASAIO Journal 2000, p. 268, and the disclosure of which is incorporated herein by reference.

In fluidized form, the inventive composite ECMs can also find use in an endoscopic injection procedure to correct vesicureteral reflux. In such applications, a submucosal injection can be made, for instance in the area under the ureteral orifice of a patient, to induce smooth muscle growth and collagen formation at the injection site.

It is contemplated that tissue graft constructs formed with composite ECMs of the present invention can be used in neurological applications. For example, in techniques requiring a dural substitute to repair defects due to trauma, tumor resection, or decompressive procedures.

In addition to in vivo uses, it is anticipated that ECM composites of the invention can be utilized as cell growth substrates for in vitro cultivation of eukaryotic or other cells. These applications employ techniques in the art which have been applied to other naturally-derived ECMs or synthetic graft materials and can be similarly undertaken using the composite ECMs of the present invention. Typically, the composite ECM composition will be combined with various nutrients, growth factors, minerals and salts known in the art to be important for the particular cell types.

The inventive composite ECMs can also serve as a collagenous matrix in compositions for producing transformed cells. The techniques for cell transformation have been described in International Publication Nos. WO 96/25179 and WO 95/22611; the disclosures of which are expressly incorporated herein by reference. Preferably, purified composite ECMs of the present invention, for example in fluidized or paste form, is included in the cell transformation compositions, in combination with a recombinant vector (e.g. a plasmid) containing a nucleic acid sequence with which in vitro or in vivo target cells are to be genetically transformed.

For the purpose of promoting a further understanding of the present invention, the following specific Experimental is provided. It will be understood that this Experimental is illustrative, and not limiting, of the present invention.

EXPERIMENTAL 1

Summary

Human umbilical vein endothelial cells (HUVEC) were grown for two weeks on [ptvomr SIS and then removed to leave behind intact human basement membrane materials. The resulting composite ECM material was termed "conditioned" SIS (c-SIS). When re-seeded on c-SIS, HUVEC exhibited enhanced organization of cell junctions and had increased metabolic activity compared to cells on native SIS (n-SIS). HUVEC grown on c-SIS also released lower amounts of the pro-inflammatory prostaglandin $PGI_2$ into the media compared to cells grown on n-SIS. Additionally, adhesion of resting or activated human platelets to c-SIS was significantly decreased as compared to n-SIS. Conditioning of porcine SIS by human endothelial cells was thus demonstrated to improve key biological properties of the material. Statistical analysis for this Experimental was made by ANOVA and $p<0.05$ was considered significant.

1.1 Materials and Methods 1.1.1 Cell Culture and SIS

Human umbilical vein endothelial cells (HUVEC) were obtained from Clonetics (East Rutherford, N.J.) and grown in endothelial growth media EGM (Clonetics). EGM contains 2% fetal bovine serum, 12 .tg/ml bovine brain extract, I μg/ml human epidermal growth factor, and I μg/ml hydrocortisone, getamicin, and amphotericin B. HUVEC were maintained at 5% $CO_2$ at 37° C., and passages 1-4 were used for experiments.

SIS was obtained from Cook Biotech, Inc. (West Lafayette, Ind.) in a dehydrated form and was rehydrated in endothelial basal media (EBM; Clonetics) at 37° for at least 10 min. Once hydrated, the SIS was fastened to wells with an approximate area of 0.44 $cm^2$ available for cell seeding.

1.1.2 Confocal Microscopy

Samples of SIS for confocal microscopy were rinsed twice in phosphate-buffered saline (PBS) and fixed in 4% paraformaldehyde for 15 minutes, rinsed extensively in PBS, permeabilized using 0.2% TritonX-100 and labeled with appropriate antibodies. For visualization by confocal microscopy, samples were mounted on glass slides with Fluoromount-G™ (Southern Biotechnology Associates Inc., Birmingham, Ala.). For evaluation of cell spreading and cell-cell junction formation on individual human matrix proteins, acid washed glass slides were coated with the following concentrations of matrix proteins for 16 hours: 10 tg/ml human collagen (type I) (Chemicon International, Temecula, Calif.); 10 μg/ml human fibronectin (Sigma Chemcial Co., St. Louis, Mo.); 1/5 .tg/ml human laminin (Sigma Chemical Co., St. Louis, Mo.); 0.5 tg/ml human vitronectin (Chemicon International, Temecula, Calif.). For experiments on glass slides coated with human matrix proteins, HUVECs at passage 2 were seeded onto the glass slides at 75,000 cells/mm$^2$ and cultured for 72 hours prior to fixation with 4% paraformaldehyde. Visualization of cell-cell adherens was made using mouse anti-βcatenin (Zymed Laboratories Inc., San Francisco, Calif.); tyrosine phosphorylated proteins were visualized using a mouse anti-phosphotyrosine antibody (Transduction Laboratories, Lexington, Ky.). Actin filaments were visualized using Texas-Red Phalloidin (Molecular Probes, Eugene, Oreg.). Secondary antibodies used were FITC-conjugated AffiniPure Donkey Anti-Rabbit IgG (H+L) and FITC-conjugated AffiniPure Goat Anti-Mouse IgG (H+L) (Jackson ImmunoResearch Laboratories, Inc., West Grove, Pa.). Samples were observed and recorded using Confocal Laser Microscopy.

1.1.3 Western Blot Analysis

Cells were harvested by direct lysis in sodium dodecyl sulfate (SDS) gel sample buffer. Protein concentrations were determined using the amido black method Sheffield J B, Graff D, Li H P. A solid-phase method for the quantitation of protein in the presence of sodium dodecyl sulfate and other interfering substances. Anal Biochem 1987; 166(1):49-54. Equal protein (30 μg) was loaded onto a 10% SDS-polyacrylamide gel for separation and transferred to nitrocellulose for immunoblot analysis. The same primary antibodies used in immunocytochemistry experiments as well as anti-mitochondrial glycosylase (ab6491) (Abcam Ltd, Cambridge, UK) along with the appropriate horseradish peroxidase-labeled secondary antibodies obtained from Jackson Immunoresearch (West Grove, Pa.) were used. Each experiment was conducted at least in triplicate.

For analysis of basement membrane protein deposition, SIS was minced into tiny sections and extracted in SDS gel sample buffer. These samples were then boiled and centrifuged at 14,000×g for 10 minutes. The supernatant was collected and the remaining pieces of SIS were discarded. Protein levels were equalized by amido back assays and loaded onto a 5% SDS-PAGE gel for separation and transferred to nitrocellulose for immunoblot analysis. Human fibronectin was detected using rabbit anti-human fibronectin (Cederlane Laboratories, Ltd., Ontario, Canada) with the appropriate horseradish peroxidase-labeled secondary antibodies (Jackson Immunoresearch, Inc.).

1.1.4 Preparation of Conditioned SIS

A procedure developed by Gospadarowicz (Gospadarowicz D., Preparation of extracellular matrices produced by cultured bovine corneal endothelial cells and PF-HR-9 endodermal cells: their use in cell culture. In: Barnes D W, Sirbasku D A, Stao G H, editors. Methods for preparation of media. Supplements and Substrata. New York: Alan R Liss; 1984. p. 275-93) was used to remove HUVEC from SIS with minimal disruption to the basement membrane deposited by the cells. HUVEC were seeded at 100,000 cells/cm$^2$ and grown on SIS for two weeks and then rinsed several times in PBS. 20 mM solution of high-grade ammonia hydroxide (NH$_4$OH) (Mallinckrodt AR Select Cat #6665) at 40° C. was placed in each well for approximately 10 minutes in situ. Wells were then rinsed several times with sterile water and vigorously mixed to remove all cells from the SIS. Native SIS (n-SIS) was also subjected to the same cell-stripping protocol used to prepare c-SIS.

1.1.5 Verification of Cell Removal

Removal of all HUVEC was verified when preparing c-SIS visually using fluorescence microscopy and scanning electron microscopy (SEM), and biochemically by immunoblot analysis. For fluorescence microscopy, samples were fixed in 4% paraformaldehyde for 15 min and then stained with Hoechst 33258 nuclear staining dye obtained from Molecular Probes (Eugene, Oreg.). Images of stained cell nuclei were viewed and recorded on an RT Color Spotlights camera (Diagnostic Instruments, Sterling heights, Mich.) using an Optiphot-2 Nikon epifluorescent microscope. For SEM, samples were prepared by fixation in 4% gluteraldehyde, dehydrated through increasing ethanol concentrations to 100% ethanol, sputter coated with gold and viewed using a JOEL scanning electron microscope. For immunoblot analysis, the surface of SIS was scraped directly in SDS sample buffer and an antibody specific for the cellular enzyme anti-mitochondrial-8-oxoguanine DNA-glycosylase (ab6491), Abcam Limited (Cambridge, UK) or for (β-catenin along with the appropriate horseradish peroxidase-labeled secondary antibodies (Jackson) was used to detect the presence of cells on SIS.

1.1.6 Cell Adhesion Assays

Cell adhesion to SIS was measured using metabolically labeled HUVEC. Cells were grown in 150 mm$^2$ tissue culture dishes and labeled for 16 hours in 25 μCi of $^{35}$S-methionine, rinsed in PBS and then removed from the dish using trypsin. $^{35}$S-methionine labeled HUVEC were resuspended in growth media and equal numbers of cells (100,000/cm$^2$) were added to n-SIS or c-SIS and allowed to adhere for varying lengths of time as indicated. After the adhesion period, SIS was washed with PBS to remove unbound cells and the amount of radioactivity remaining on the SIS was measured using a liquid scintillation counter.

1.1.7 Metabolic Activity Assessment

To estimate the relative metabolic rates of cells grown on n-SIS and c-SIS, cells were seeded at 100,000 or 200,000 cells/cm$^2$ and cultured for one hour to two weeks. Metabolic activity was assessed using CellTiter 96 Aqueos Once Solution Cell Proliferation Assay obtained from Promega (Madison, Wis.). The assay is a calorimetric method, which measures the amount of NADPH produced by dehydrogenase enzymes in metabolically active cells by determining the amount of colored reaction product (Formazan) that can be produced from MTS tetrazolium compound (Owen's reagent) in media samples. 200 μL of a solution containing 20 μL of CellTiter 96 Aqueous Once Solution Reagent was added to 100 μL of culture media and incubated at 37° C. for 3 hours according to the manufacturer's instructions. After 3 hours OD$_{490}$ was recorded on an ELISA plate reader.

1.1.8 Prostacyclin Measurement

Prostacyclin release was measured by incubating SIS wells in 200 μL of EGM media for 1 hour. The media was collected and centrifuged at 14,000×g for 2 min to pellet any particulates, and the supernatant was retained for prostacyclin measurement. 6-keto Prostaglandin Fi$_a$EIA kit was obtained from Cayman Chemical (Ann Arbor, Mich.) and used to determine the amount of PGI$_2$ present in each sample.

1.1.9 Platelet Adhesion Assays

Preparation of Platelets: Whole blood was drawn by venipuncture from healthy aspirin-free human donors and collected in ACD (83 mM soduim citrate, 111 mM glucose, 71.4 mM citric acid, ph 4.5; 1:7, v/v). Platelet-rich plasma was isolated by centrifugation at 250 g for 20 min, and prostaglandin E1 (0.1 mM) or prostaglandin 12 (50 ng/ml) was added. The platelet-rich plasma was centrifuged for 15 min at 850×g, and the platelets were resuspended in Hepes-buffered saline ((Buffer A) 10 mM Hepes, pH 7.4, 138 mM NaCl, 12 mM NaHCO3, 10 mM KCI, 5.5 mM glucose, 0.35% BSA, 2 units/ml heparin and I unit/ml apyrase). Resuspended platelets were washed three times in Buffer A without BSA or inhibitors and the concentration was adjusted to $(0.5\text{-}1.0) \times 10^9$ platelets/ml. The platelets were then labeled with $^{51}Cr$ (0.5 mCi) for 60 min. They were washed 2 times in Buffer A without inhibitors. For platelet activation, to 6-8 ml of resuspended platelets, 2 units of thrombin were added. $^{51}Cr$-labeled platelets were allowed to incubate for 1 hour at room temperature, and then platelets were aspirated off, followed by a subsequent 5 mL PBS wash. Adherent platelets were lysed using 2004 of 2% SDS twice. The lysates were collected, and a y counter was used to determine the radioactivity in each sample. All means calculated have 6 replicates.

1.2 Results 1.2.1 Characterization of HUVEC Growth on Native SIS

Figure 4:
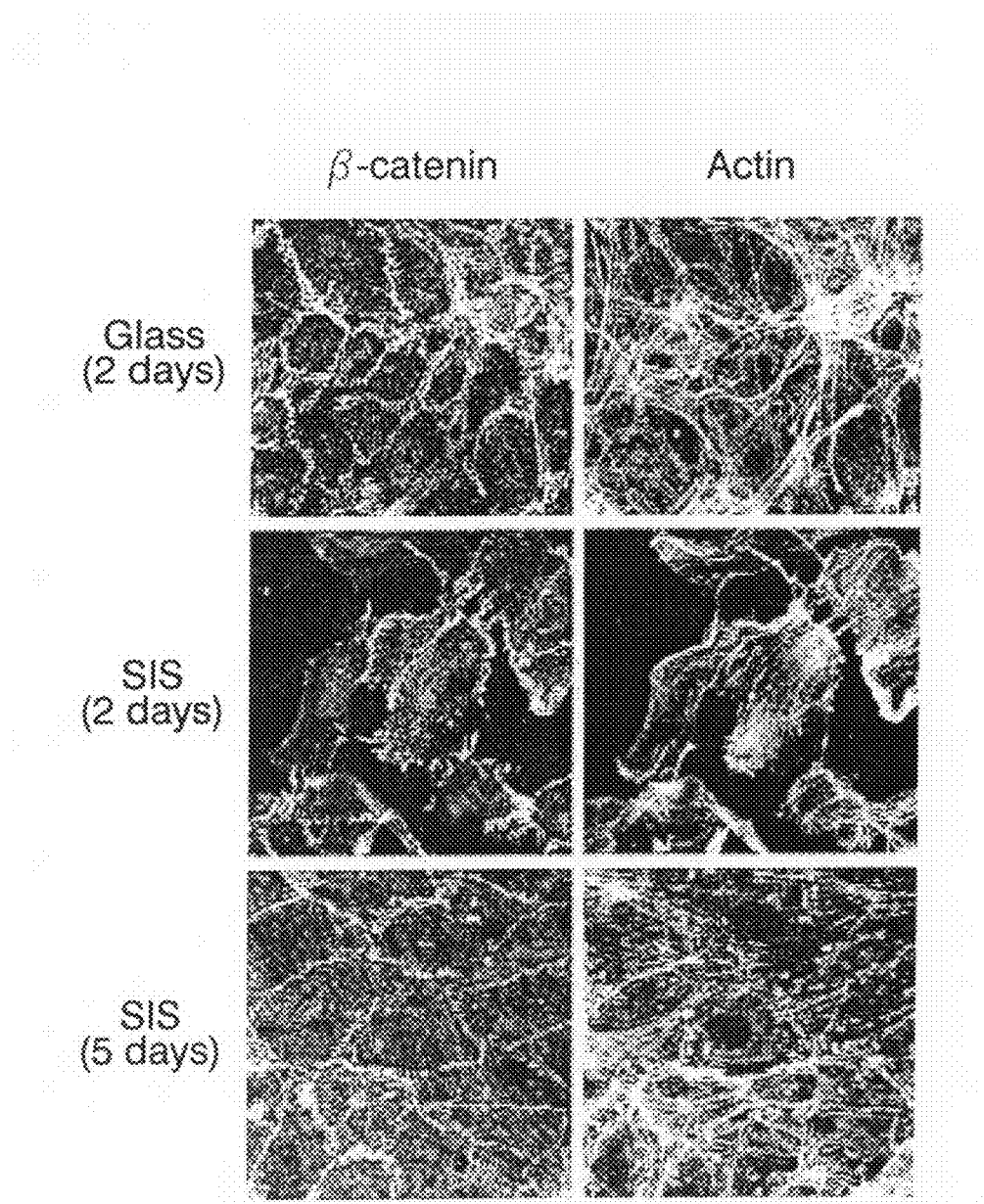
FIG. 4. HUVEC grown on SIS form a confluent monolayer more slowly than when grown on glass slides. HUVEC were seeded onto glass slides or untreated SIS at a concentration of 100,000 cells/mm$^2$ and analyzed by immunofluorescence confocal microscopy to determine the length of time needed for cells to form a confluent monolayer. Cells were labeled with a mouse monoclonal antibody against ~3-catenin followed by an anti-mouse Ig antibody conjugated to FITC to visualize cell-cell junctions. Cells were also labeled with phalloidin conjugated Texas-Red to visualize filamentous actin. Bar=20 microns.

To examine HUVEC growth on SIS, cells were seeded at a density of 100,000 cells/cm$^2$ and allowed to grow for various lengths of time. FIG. 4 shows confocal microscope images illustrating the appearance of HUVEC on SIS and glass at various times after seeding using an antibody against the cell-cell junction protein (β-catenin, followed by FITC-labeled secondary antibody and with Texas-Red-phalloidin to visualize actin. HUVEC grown on glass slides were confluent by 2 days after seeding and exhibited a typical cobblestone appearance characteristic of endothelial cells in culture and similar to the morphology of endothelial cells in vivo (Fun-YC, Biomechanics: Motion, Flow, Stress, and Growth. 1990, New York: Springer-Verlag New York Inc. 196-225.) However, HUVEC grown on SIS at the same initial seeding density of 100,000 cells/mm$^2$ for 2 days did not form a confluent monolayer with well-developed cell-cell junctions. We found that 5 days after seeding, HUVEC formed a confluent monolayer when grown on SIS.

1.2.2. HUVEC Conditioned SIS

Figure 5A:
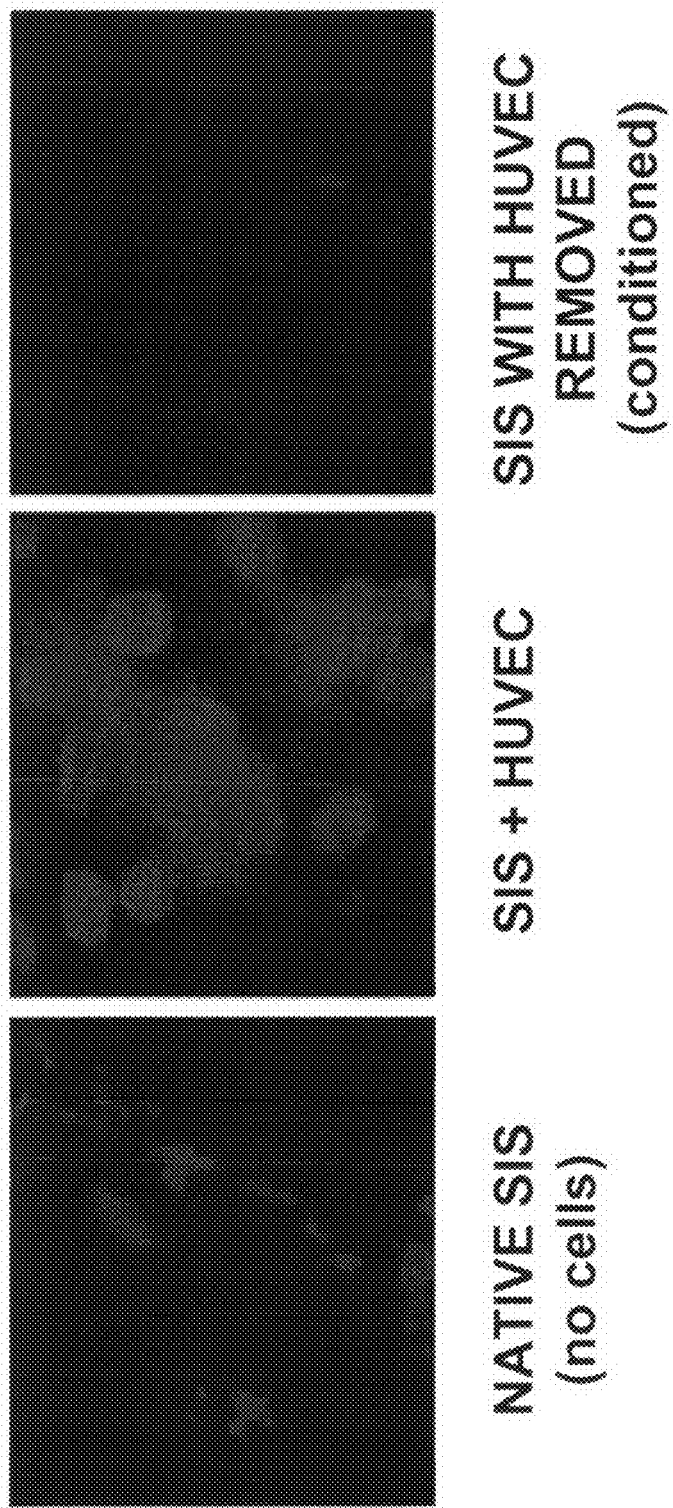
FIG. 5. HUVEC are efficiently removed from SIS following "conditioning." Native SIS without cells, SIS with HUVEC grown for 14 days, and SIS with HUVEC grown for 14 days and then removed (conditioned) were stained with Hoechst dye to label cell nuclei and viewed in the fluorescence microscope (A) or analyzed by immunoblotting using antibodies against either of two cellular proteins, β-catenin or mitochondrial glycosylase (B). Both visual (microscopy) and biochemical (immunoblot) analysis demonstrate that no cells are detected on the SIS following the conditioning treatment.
Figure 5B:
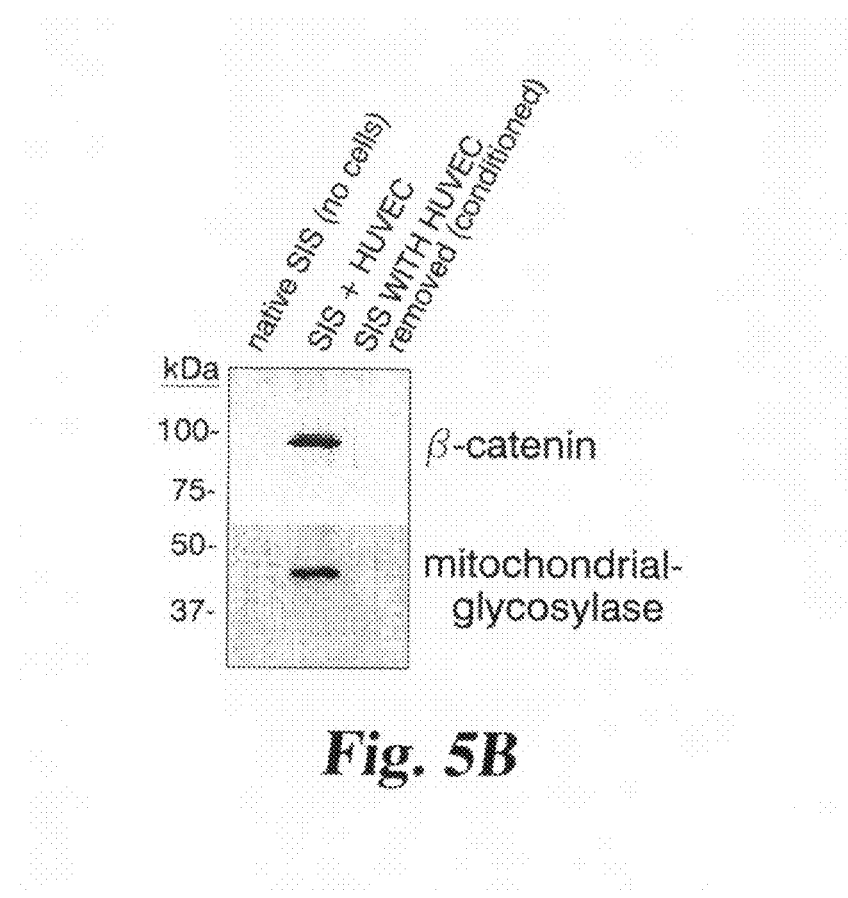

HUVEC were seeded on SIS and grown for 14 days to allow sufficient time for the cells to deposit human matrix proteins onto the surface of the porcine SIS. Thus, HUVEC were cultured for approximately 9 days after reaching confluency. HUVEC were then removed from the SIS using NH4OH as has been described previously (Gonzales M, Weksler B, Tsuruta D, Goldman R D, Yoon K J, Hopkinson S B, Flitney F W, and Jones J C. Structure and function of a vimentin-associated matrix adhesion in endothelial cells. Mot Biol Cell 2001; 12(1): 85-100) to prepare extracellular matrices from endothelial cells according to a procedure originally described by Gospodarowicz (Gospodarowicz D., Preparation of extracellular matrices produced by cultured bovine corneal endothelial cells and PF-HR-9 endodermal cells: their use in cell culture. In: Barnes D W, Sirbasku D A, Stao G H, editors. Methods for preparation of media. Supplements and Substrata. New York: Alan R Liss; 1984. p. 275-93). This process was referred to as "conditioning" of the SIS and resulted in a composited ECM material having a non-human (porcine) ECM base layer having human ECM substances deposited in a substantial layer or coating on the base layer. For all experiments, native SIS (n-SIS) was treated with the same cell removal protocol. FIG. 5A shows microscopy images of untreated SIS, SIS with cells grown for 14 days and left intact, and SIS with cells removed (conditioned) that were stained with Hoechst dye to label cell nuclei to verify that all cells were removed from the SIS. Confirmation that all cells were removed was also made by immunoblotting for the cellular proteins (3-catenin and mitochondrial-DNA8-oxanine-glycosylase (FIG. 5B).

Figure 6:
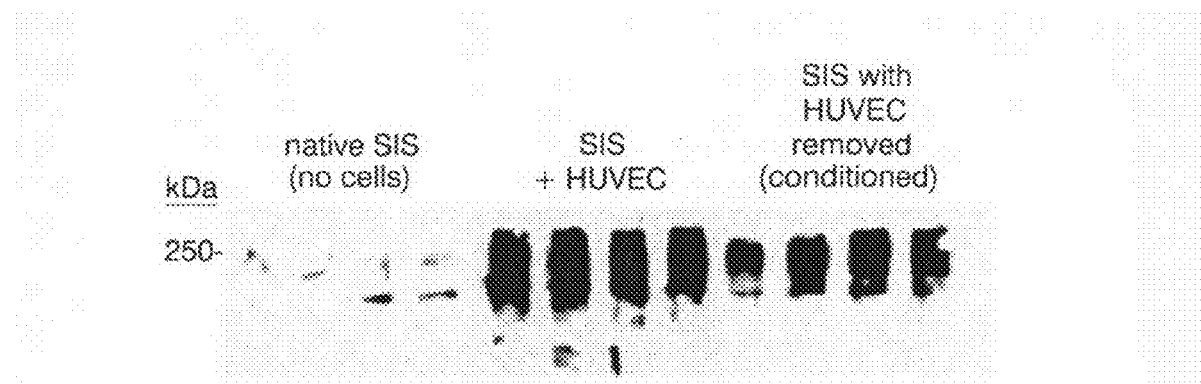
FIG. 6. HUVEC deposit human fibronectin onto the surface of conditioned SIS. Immunoblot analysis of native SIS without cells, SIS with HUVEC grown for 14 days, and SIS with HUVEC grown for 14 days and then removed (conditioned) using an antibody that is specific for human fibronectin and has little or no cross reactivity with porcine fibronectin. Human fibronectin deposited by HUVEC is retained on the conditioned SIS following removal of the cells.
Figure 7:
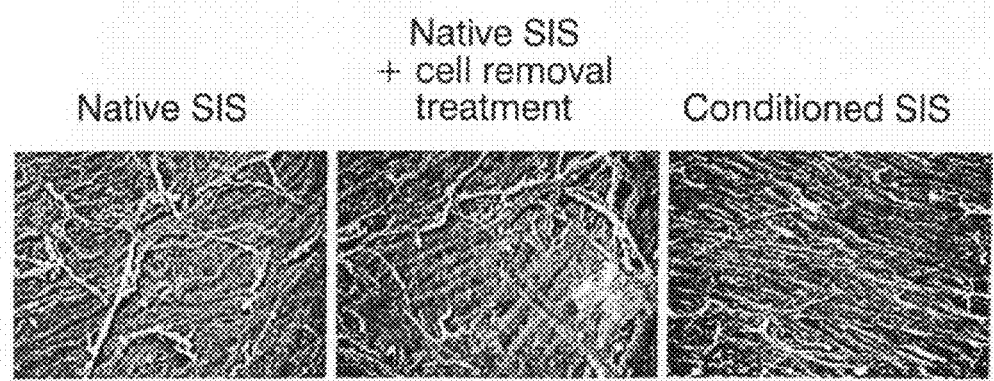
FIG. 7. Scanning electron microcopy of the surface of SIS. SEM of untreated SIS, native SIS (subjected to the NH$_4$OH cell removal treatment) and conditioned SIS indicted there was no obvious structural damage to the SIS as a result of the cell removal treatment.

To demonstrate that HUVEC deposit proteins remained biosynthetically associated with SIS, an antibody specific for human fibronectin (hFN) was identified that did not cross-react with the porcine fibronectin. Western blot analysis revealed that after allowing HUVEC to be grown and cultured on n-SIS for two weeks and then removed, hFN was detected on the surface in the absence of cells. FIG. 6 shows a western blot to illustrate the presence of hFN on the surface of SIS following the conditioning treatment. An antibody specific for human laminin that did not cross-react with porcine laminin was also used. In this work, no evidence of secretion of laminin onto conditioned SIS was found (not shown). To verify that the cell removal treatment did not cause obvious structural damage to the SIS, scanning electron microscopy (SEM) was used to visualize the SIS surface (FIG. 7). SEM of native SIS subjected to the cell removal treatment and of conditioned SIS demonstrated that the SIS surface was not structurally damaged by the cell removal treatment in comparison to native SIS that did not undergo the cell removal treatment.

1.2.3 HUVEC Attachment is not Different on c-SIS Compared to n-SIS

Figure 8:
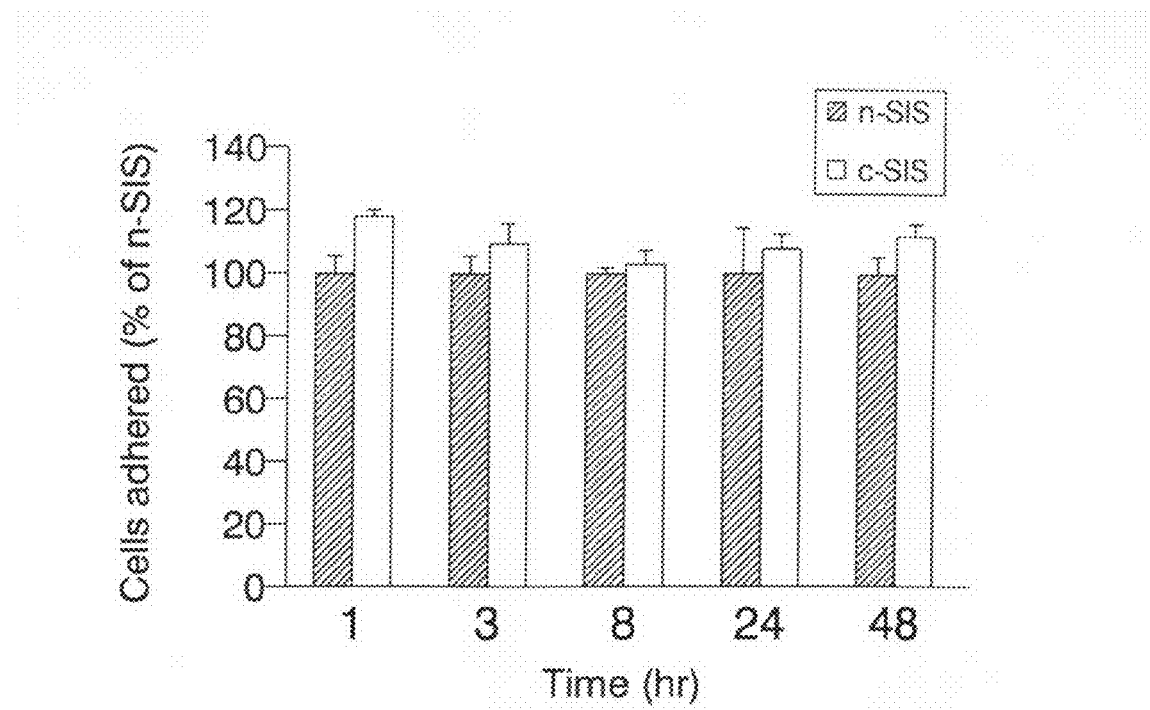
FIG. 8. Cell attachment assays on native and conditioned SIS. HUVEC were labeled with 35S-methonine overnight and then seeded onto native and conditioned SIS to determine if there was a difference in the relative number of cells that were able to adhere to the two surfaces. There was no statistically significant difference in the relative numbers of HUVEC adhered to native or conditioned SIS at times ranging from 1 to 48 hr after seeding.

Materials were next evaluated to determine whether there was a difference in initial cell adhesion during the first 1-48 hours after seeding HUVEC onto n-SIS and c-SIS (FIG. 8). HUVEC growing on tissue culture plastic were labeled with $^{35}S$-methionine for 18 hours during log phase growth to allow incorporation of the radioactive label into newly synthesized proteins. The cells were washed free of unincorporated radioactivity in the media and the labeled cells were collected by brief trypsinization. Equal numbers of cells were seeded onto n-SIS or c-SIS and allowed to adhere. At each time point examined, unbound cells were washed away and the adherent cells were fixed to the SIS using 4% paraformaldehyde and bound radioactivity was measured using a y-counter. FIG. 8 shows there were no statistically significant differences in the number of cells present on n-SIS vs. c-SIS at any of the time points examined between 1 and 48 hours.

1.2.4 Growing HUVEC on c-SIS Improves Cell-Cell Function Organization

Figure 9:
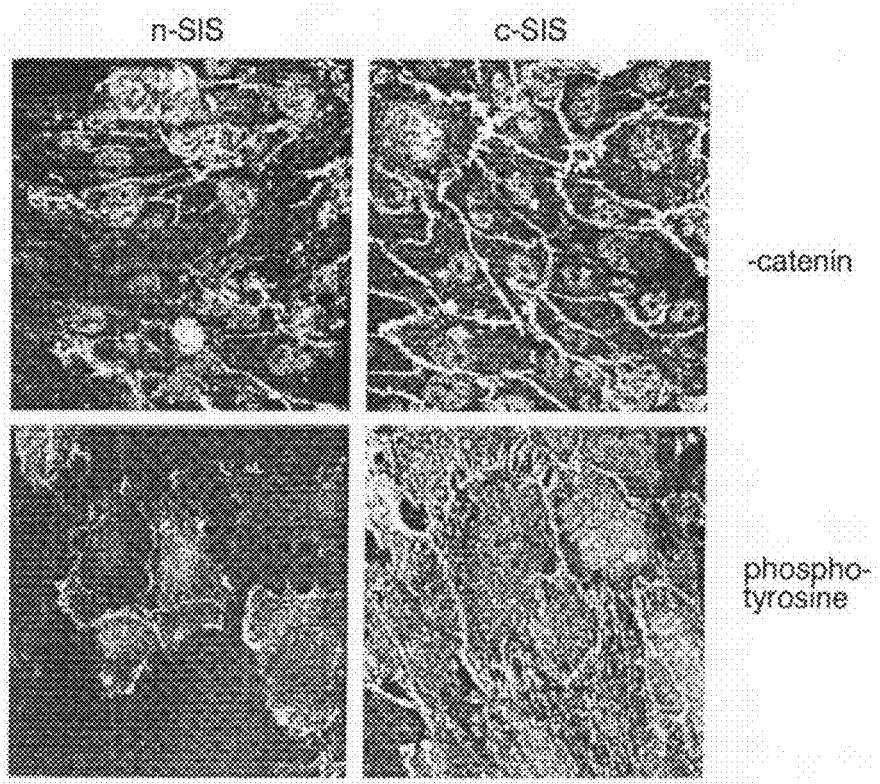
FIG. 9. Formation of cell-cell adherens junctions is improved in HUVEC grown on conditioned SIS compared to cells grown on native SIS. HUVEC were seeded onto native or conditioned SIS at a concentration of 100,000 cells/cm2 and analyzed by immunofluorescence confocal microscopy 48 h after seeding. Cells were labeled with a mouse monoclonal antibody against β-catenin or with mouse monoclonal antibody against phosphotyrosine containing proteins followed by an anti-mouse Ig antibody conjugated to FITC to visualize cell-cell junctions. Cells grown on conditioned SIS form well organized cell-cell cell junctions as indicated by the appearance of β-catenin staining at the membrane whereas cells grown on native SIS have patchy, discontinuous membrane staining. Phosphotyrosine staining, which can be an indicator of active cell-cell and cell-matrix signal transduction activity, is also more abundant in cells grown on conditioned SIS compared to native SIS.

We next sought to determine if there were any differences in the morphological characteristics of HUVEC grown on n-SIS vs. c-SIS. FIG. 9 illustrates the dramatic improvement in the organization of cell-cell junctional complexes (adherens junctions) when cells are grown on c-SIS compared to cells grown on n-SIS at 48 hours after seeding. Cells were labeled for (3-catenin and for phosphotyrosine containing proteins and imaged using confocal microscopy.

Cells grown on n-SIS appeared to be visible in multiple different focal planes indicating the surface of n-SIS was relatively rough. In contrast, cells grown on c-SIS were visible across the surface of the SIS primarily within a single focal plane suggesting that conditioning of the SIS might modify the surface of the SIS by deposition of a layer of matrix proteins that creates a smooth surface that allows cells to spread more uniformly. This result suggests that SIS conditioned with human basement membrane proteins provides an improved substrate for the establishment of endothelial monolayers with well-organized cell-cell junctions.

1.2.5 Metabolic Activity of HUVEC is Higher on c-SIS

To evaluate the metabolic activity of HUVEC grown on n-SIS and c-SIS, metabolic activity assays, which measured the production and release of NADPH into the culture media, were conducted. HUVEC were seeded onto n-SIS and c-SIS (100,000 cells/cm$^2$ and 200,000 cells/cm$^2$) and allowed to grow over a period of 1 hour to 240 hours. At both seeding densities, HUVEC grown on n-SIS exhibited a significant decrease in NADPH production after 24 and 96 hours in culture, despite the fact equal numbers of cells adhered to n-SIS and c-SIS (see FIG. 8), when compared to their initial (1 hour) levels (FIG. 10). In sharp contrast, HUVEC grown on c-SIS exhibited a significant increase in NADPH production after 24 hours in culture. NADPH production by HUVEC remained significantly higher in cells grown on c-SIS compared to n-SIS through the first 96 hours. By 168 hours culture, NADPH levels were not different between groups; after 240 hours in culture NADPH production had dropped significantly below initial levels for both substrates and were not significantly different from each other.

1.2.6 PGI$_2$ Production is Reduced when HUVEC are Grown on c-SIS

To evaluate the inflammatory response of HUVEC grown on n-SIS and c-SIS, production and release of the inflammatory prostaglandin, prostacyclin (PGh), was measured using an enzyme-linked immunosorbant assay (EIA). HUVEC were seeded at an initial density of 100,000 cells/cm$^2$ and grown on n-SIS or c-SIS for 24 or 48 hours. After 24 or 48 hours, fresh media was incubated with the wells for 1 hour and the media was collected. Significantly higher levels of PG1$_2$ were released into the media by cells grown on n-SIS compared to cells grown on c-SIS (FIG. 11). This difference (approximately 3-fold more PGI2 (pg/mL) than HUVEC on c-SIS, increased to approximately 4-fold at the 48 hour time point.

1.2.7 Platelet Adhesion is Reduced on c-SIS

Figure 12A:
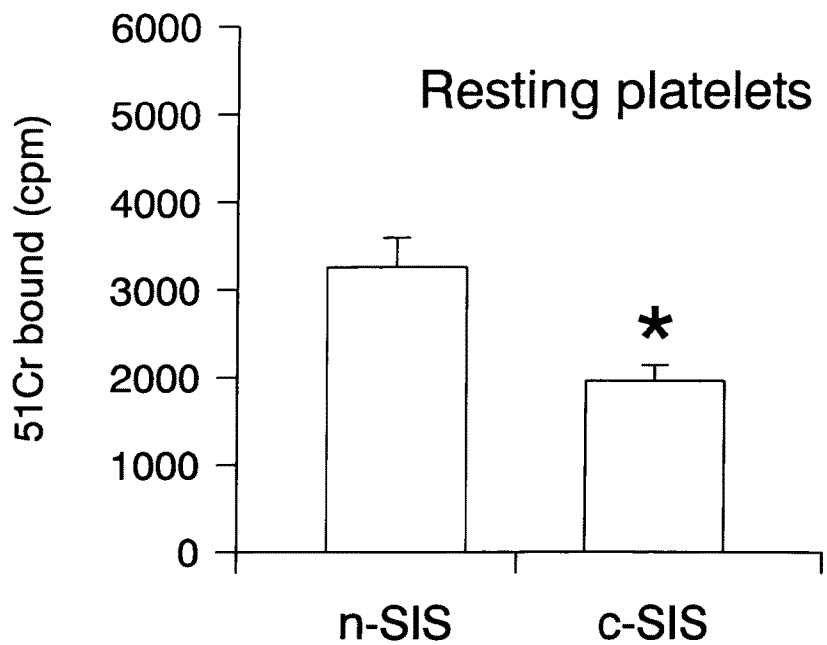

To determine whether conditioning of SIS might affect the thrombogenic potential of SIS, platelet adhesion assays were performed. Using freshly isolated human platelets, we found that conditioning the SIS resulted in a significant decrease in platelet adhesion of approximately 40% when compared to n-SIS (FIG. 1 12A). This value of a 40% decrease was typical of four independent experiments using platelets from multiple donors in which the decrease in platelet adhesion on c-SIS ranged from 30-43%. In each independent experiment this decrease was statistically significant ($p<0.05$ by ANOVA). Interestingly, platelet adhesion was also decreased (by approximately 21-26%) on SIS with HUVEC still present, compared to n-SIS, but this difference was not statistically significant in any of four independent experiments (data not shown).

Figure 12B:
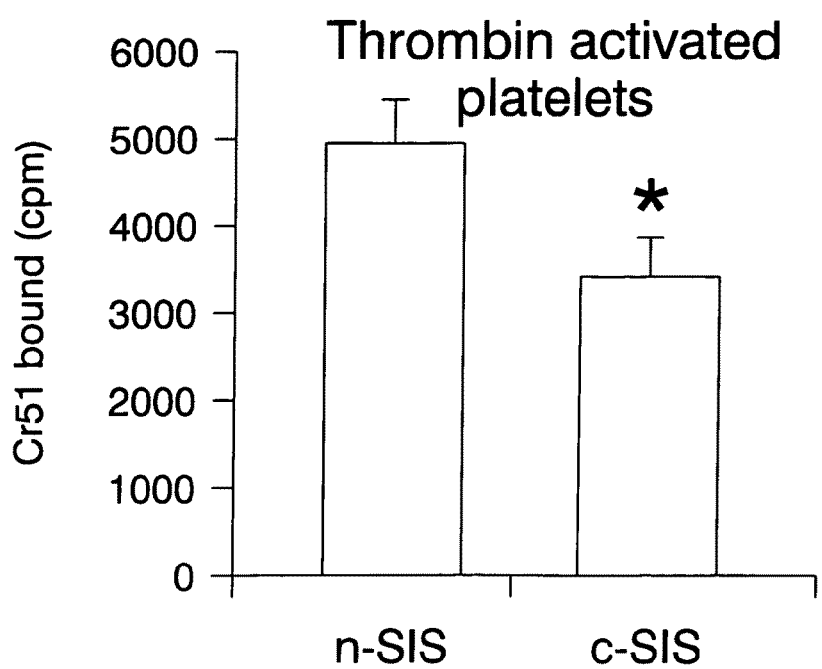

The platelet adhesion assay was repeated using platelets that were activated by the addition of thrombin to more accurately mimic the conditions likely found in the vicinity of an implanted graft (FIG. 12B). When compared to n-SIS, c-SIS significantly reduced adhesion of activated platelets by approximately 30%. As with unactivated platelets, in each of four independent experiments, adhesion of thrombin-activated platelets to SIS with HUVEC still present was consistently lower by 15-20%, but this difference was not statistically significant. n-SIS was also coated with commercially available human fibronectin to determine if coating with this single ECM protein known to be present in c-SIS could mimic the decrease in platelet adhesion seen on c-SIS. Although coating n-SIS with human fibronectin consistently reduced platelet adhesion by approximately 6-15% in each of three independent experiments compared to uncoated nSIS, this difference failed to consistently achieve statistical significance (not shown).

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited in this application are indicative of the abilities possessed by those of ordinary skill in the pertinent art and are hereby incorporated by reference in their entirety as if each had been individually incorporated by reference and fully set forth.

What is claimed is:

1. A medical graft material, comprising an extracellular matrix composite including a first naturally derived extracellular matrix material having a surface, and a second, biosynthetically-deposited extracellular matrix material on said surface, wherein the second extracellular matrix material is secreted by cells onto the first extracellular matrix material, wherein the second, biosynthetically-deposited extracellular matrix material is secreted by cells which are xenogenic to the first extracellular matrix material wherein the second extracellular matrix material contains extracellular matrix components that are exogenous with respect to the first extracellular matrix material, and wherein said medical graft material is free of living cells.

2. The medical graft material of claim 1, wherein said second extracellular matrix material comprises one or more fiber-forming proteins.

3. The medical graft material of claim 2, wherein the one or more fiber-forming proteins include collagen and/or elastin.

4. The medical graft material of claim 1, wherein said second extracellular matrix material comprises one or more adhesive proteins.

5. The medical graft material of claim 4, wherein said adhesive proteins comprise fibronectin and/or laminin.

6. The medical graft material of claim 1, wherein the first extracellular matrix material comprises submucosa.

7. The medical graft material of claim 6, wherein the submucosa is intestinal, urinary bladder or stomach submucosa.

8. The medical graft material of claim 7, wherein the submucosa is small intestinal submucosa.

9. The medical graft material of claim 1, wherein the first extracellular matrix material is from a warm-blooded vertebrate.

10. The medical graft material of claim 1, wherein the second extracellular matrix material is human.

11. The medical graft material of claim 1, wherein the second extracellular matrix material is secreted by one or more of endothelial cells, muscle cells, fibroblast cells, mesothelial cells, pericyte cells, macrophage cells, monocyte cells, plasma cells, mast cells, adipocyte cells, chondrocyte cells, stem cells, or a cell population differentiated from stem cells.

12. The medical graft material of claim 11, wherein the second extracellular matrix material contains matrix components secreted by endothelial cells.

13. The medical graft material of claim 12, wherein the endothelial cells are vascular endothelial cells.

14. The medical graft material of claim 13 which is configured for implantation in the cardiovascular system of a human.

15. The medical graft material of claim 14, which has a tubular form, and wherein at least a lumenal surface of the tubular form contains said second extracellular matrix material.

16. An extracellular matrix graft prosthesis conditioned with matrix components, comprising:
an extracellular matrix graft material; and
biosynthetically-deposited exogenous extracellular matrix components on said extracellular matrix graft material, wherein the exogenous extracellular matrix components are secreted by cells onto the extracellular matrix graft material, and wherein said graft prosthesis is free of living cells and in a dried condition, and wherein said medical graft prosthesis is packaged in a sterile sealed package.

17. A graft prosthesis of claim 16, wherein said extracellular matrix graft material comprises a submucosa, dura mater, pericardium, serosa, peritoneum, or basement membrane matrix material.

18. A graft prosthesis of claim 17, wherein said extracellular matrix graft material comprises submucosa.

19. A graft prosthesis of claim 18, wherein said submucosa is mammalian submucosa.

20. A graft prosthesis of claim 19, wherein said mammalian submucosa is porcine, bovine, or ovine submucosa.

21. A graft prosthesis of claim 20, wherein said submucosa is porcine submucosa.

22. A graft prosthesis according to claim 16, wherein said matrix components include one or more members selected from the group consisting of collagen, elastin, fibronectin, and laminin.

23. A graft prosthesis according to claim 16, wherein said prosthesis has a tubular form, and said matrix components are on at least a lumenal surface of said tubular form.

24. A graft prosthesis according to claim 16, wherein said prosthesis has a sheet form, and wherein said matrix components are deposited on a surface of at least a first side of said sheet form.

25. A graft prosthesis according to claim 16, wherein said prosthesis has multiple layers, including at least one layer of said extracellular matrix graft material.

26. A graft prosthesis according to claim 25, wherein said prosthesis has multiple layers of said extracellular matrix graft material.

27. A graft prosthesis according to claim 16, wherein said matrix components are human.

28. The extracellular matrix graft prosthesis of claim 16, wherein the extracellular matrix graft material is non-human and the extracellular matrix components are human.

\* \* \* \* \*